(12) United States Patent
Measamer et al.

(10) Patent No.: US 10,888,317 B2
(45) Date of Patent: Jan. 12, 2021

(54) CONTROL FEATURES FOR MOTORIZED SURGICAL STAPLING INSTRUMENT

(71) Applicant: Ethicon LLC, Guaynabo, PR (US)

(72) Inventors: John P. Measamer, Cincinnati, OH (US); Richard L. Leimbach, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 246 days.

(21) Appl. No.: 15/888,528

(22) Filed: Feb. 5, 2018

(65) Prior Publication Data

US 2018/0221018 A1 Aug. 9, 2018

Related U.S. Application Data

(63) Continuation of application No. 14/033,751, filed on Sep. 23, 2013, now Pat. No. 9,907,552.

(51) Int. Cl.
*A61B 17/068* (2006.01)
*A61B 17/115* (2006.01)
(Continued)

(52) U.S. Cl.
CPC ........ *A61B 17/068* (2013.01); *A61B 17/1155* (2013.01); *A61B 2017/00398* (2013.01);
(Continued)

(58) Field of Classification Search
CPC .. A61B 2090/08021; A61B 2090/0814; A61B 2090/0811; A61B 17/1155;
(Continued)

(56) References Cited

U.S. PATENT DOCUMENTS 4,805,823 A 2/1989 Rothfuss
5,205,459 A 4/1993 Brinkerhoff et al.
(Continued)

FOREIGN PATENT DOCUMENTS

CN 1827051 A 9/2006
EP 1 662 532 A1 5/2006
(Continued)

OTHER PUBLICATIONS

Chinese Office Action, First Office Action, dated Dec. 29, 2017 for Application No. CN 201480052184.4, 12 pgs.
(Continued)

*Primary Examiner* — Thomas M Wittenschlaeger
(74) *Attorney, Agent, or Firm* — Frost Brown Todd LLC

(57) ABSTRACT

An apparatus includes a body, a motorized end effector, and a control system. The end effector extends distally from the body and comprises a stapling assembly operable to drive staples into tissue. The control system is in communication with the end effector. The control system comprises a motor, a firing trigger, a switch assembly, and a movable member in communication with the firing trigger. A resilient member is engaged with the movable member. The firing trigger and the resilient member are configured to cooperate to move the movable member into engagement with the switch to thereby activate the motor. The switch assembly is configured to couple a power source with the motor to thereby activate the motor in response to actuation of the firing trigger.

20 Claims, 35 Drawing Sheets

(51) Int. Cl.
*A61B 17/00* (2006.01)
*A61B 90/00* (2016.01)

(52) U.S. Cl.
CPC ............ *A61B 2017/00734* (2013.01); *A61B 2090/0811* (2016.02); *A61B 2090/0814* (2016.02); *A61B 2090/08021* (2016.02)

(58) Field of Classification Search
CPC ........ A61B 17/068; A61B 2017/00734; A61B 2017/00398
See application file for complete search history.

(56) References Cited

U.S. PATENT DOCUMENTS

| | | | |
|---|---|---|---|
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,350,104 A | 9/1994 | Main et al. | |
| 5,415,334 A | 5/1995 | Williamson, IV et al. | |
| 5,433,721 A * | 7/1995 | Hooven ............... | A61B 17/068 227/175.1 |
| 5,465,895 A | 11/1995 | Knodel et al. | |
| 5,533,661 A | 7/1996 | Main et al. | |
| 5,597,107 A | 1/1997 | Knodel et al. | |
| 5,628,446 A | 5/1997 | Geiste et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 6,945,444 B2 | 9/2005 | Gresham et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,422,136 B1 | 9/2008 | Marczyk | |
| 7,434,715 B2 | 10/2008 | Shelton, IV et al. | |
| 7,721,930 B2 | 5/2010 | McKenna et al. | |
| 8,408,439 B2 | 4/2013 | Huang et al. | |
| 8,453,914 B2 | 6/2013 | Laurent et al. | |
| 8,632,525 B2 | 1/2014 | Kerr et al. | |
| 8,695,866 B2 | 4/2014 | Leimbach et al. | |
| 8,806,973 B2 | 8/2014 | Ross et al. | |
| 8,910,847 B2 | 12/2014 | Nalagatla et al. | |
| 8,968,276 B2 | 3/2015 | Zemlok et al. | |
| 9,005,230 B2 | 4/2015 | Yates et al. | |
| 9,028,519 B2 | 5/2015 | Yates et al. | |
| 9,161,803 B2 | 10/2015 | Yates et al. | |
| 9,713,469 B2 | 7/2017 | Leimbach et al. | |
| 9,907,552 B2 | 3/2018 | Measamer et al. | |
| 9,936,949 B2 | 4/2018 | Measamer et al. | |
| 2010/0001036 A1* | 1/2010 | Marczyk ............ | A61B 17/07207 227/175.1 |
| 2011/0006103 A1* | 1/2011 | Laurent ................. | A61B 90/30 227/176.1 |
| 2011/0011915 A1* | 1/2011 | Shelton, IV ...... | A61B 17/07207 227/176.1 |
| 2011/0155785 A1* | 6/2011 | Laurent ................ | A61B 17/068 227/180.1 |
| 2015/0083772 A1 | 3/2015 | Miller et al. | |
| 2017/0258471 A1 | 9/2017 | DiNardo et al. | |
| 2018/0221018 A1* | 8/2018 | Measamer ........... | A61B 17/068 |

FOREIGN PATENT DOCUMENTS

| | | |
|---|---|---|
| EP | 2 140 817 A1 | 1/2010 |
| EP | 2 329 773 A1 | 6/2011 |
| EP | 2 606 834 A2 | 6/2013 |
| JP | 2016-503716 A | 2/2016 |
| RU | 2098025 C1 | 10/1997 |

OTHER PUBLICATIONS

European Search Report and Written Opinion, Partial, dated Mar. 5, 2015 for Application No. EP 14185830.8, 7 pgs.
European Search Report and Written Opinion dated Jul. 6, 2015 for Application No. EP 14185830.8, 11 pgs.
European Exam Report dated Aug. 9, 2016 for Application No. EP 14185830.8, 4 pgs.
European Exam Report dated Oct. 6, 2017 for Application No. EP 14185830.8, 6 pgs.
International Search Report and Written Opinion dated Apr. 1, 2015 for Application No. PCT/US2014/056525, 19 pgs.
Japanese Office Action, Notification of Reasons for Refusal, dated May 8, 2018 for Application No. JP 2016-544014, 7 pgs.
Japanese Search Report, Search Report by Registered Searching Organization, dated Apr. 12, 2018 for Application No. JP 2016-544014, 29 pgs.
European Communication, Intention to Grant, dated May 10, 2017 for Application No. EP 14185830.8, 86 pgs.
Japanese Office Action, Notification of Reasons for Refusal, and Search Report by Registered Searching Organization dated May 8, 2018 for Application No. JP 2016-544014, 19 pgs.
Japanese Office Action, Decision to Grant a Patent, dated Aug. 7, 2018 for Application No. JP 2016-544014, 3 pgs.
Brazilian Office Action dated Feb. 14, 2020 for Application No. BR 112016006289-2, 4 pgs.
Chinese Search Report dated Dec. 19, 2017 for Application No. CN 201480052184.4, 2 pgs.
Russian Office Action, and Search Report dated May 22, 2018 for Application No. RU 2016115750, 7 pgs.
U.S. Appl. No. 16/836,291, filed Mar. 31, 2020, by DiNardo et al., entitled: "Methods and Systems for Performing Circular Stapling."
U.S. Appl. No. 16/994,101, filed Aug. 14, 2020, by Miller et al., entitled: "Staple Forming Pocket Configurations for Circular Surgical Stapler Anvil."

* cited by examiner

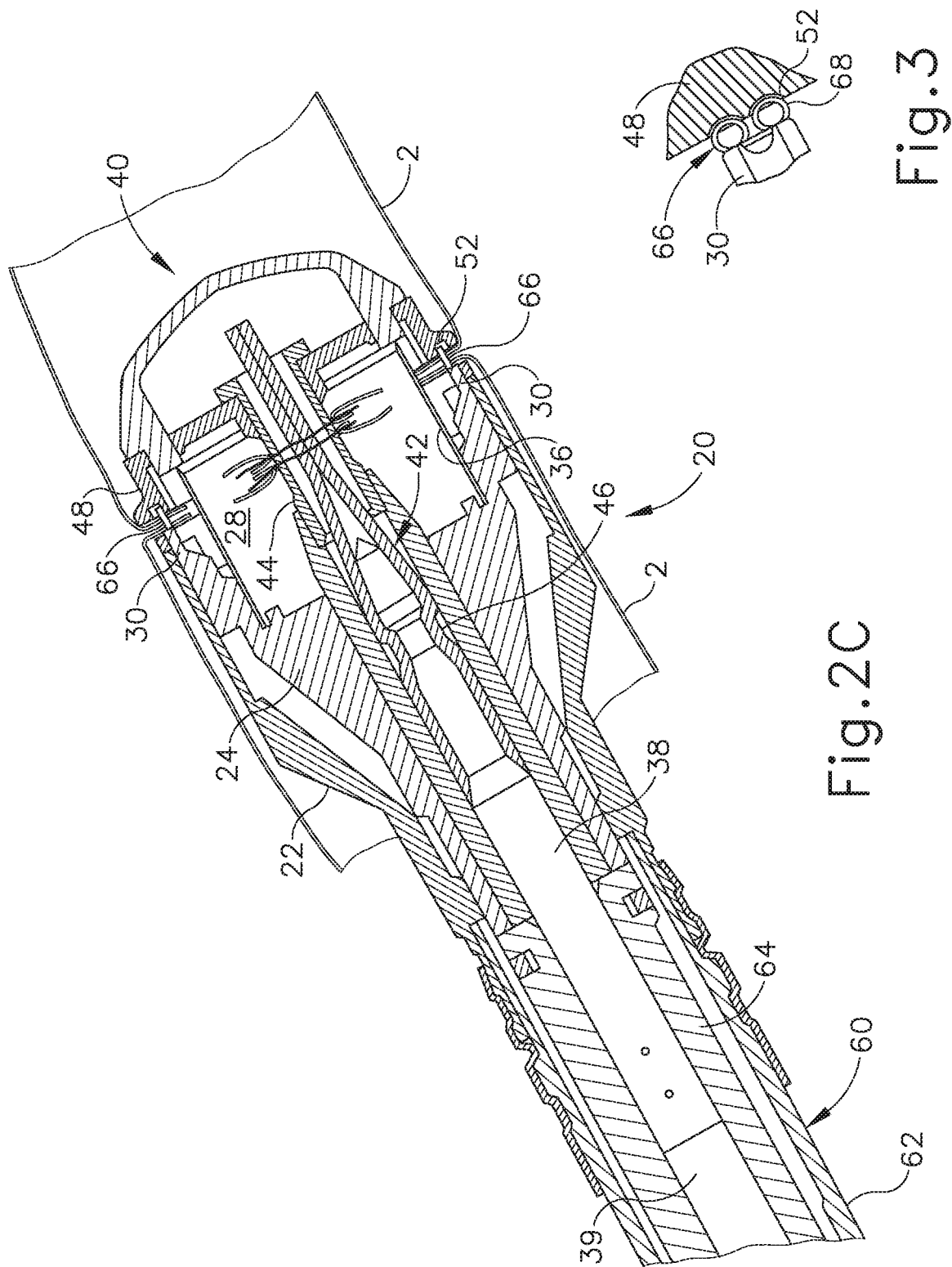

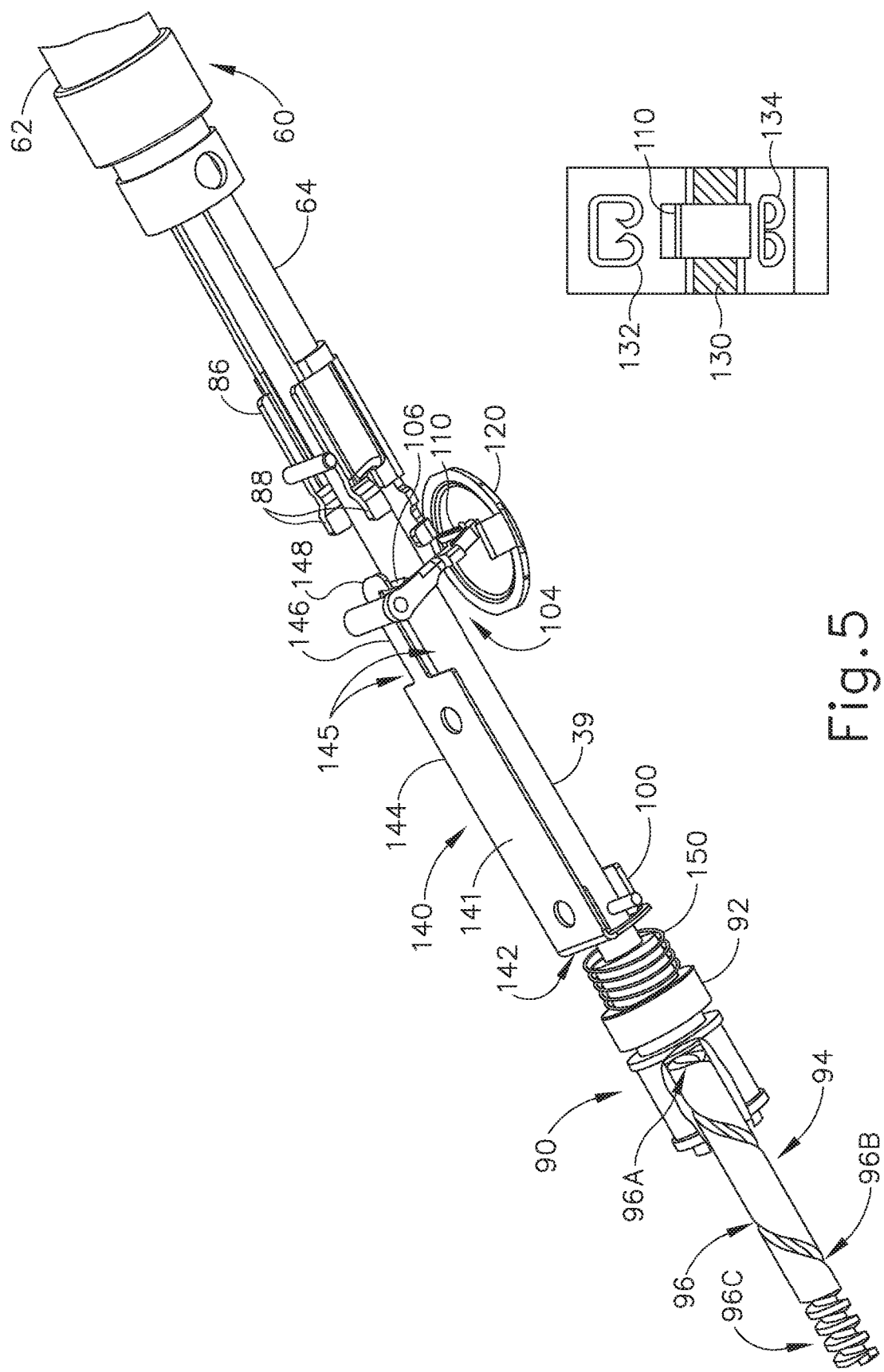

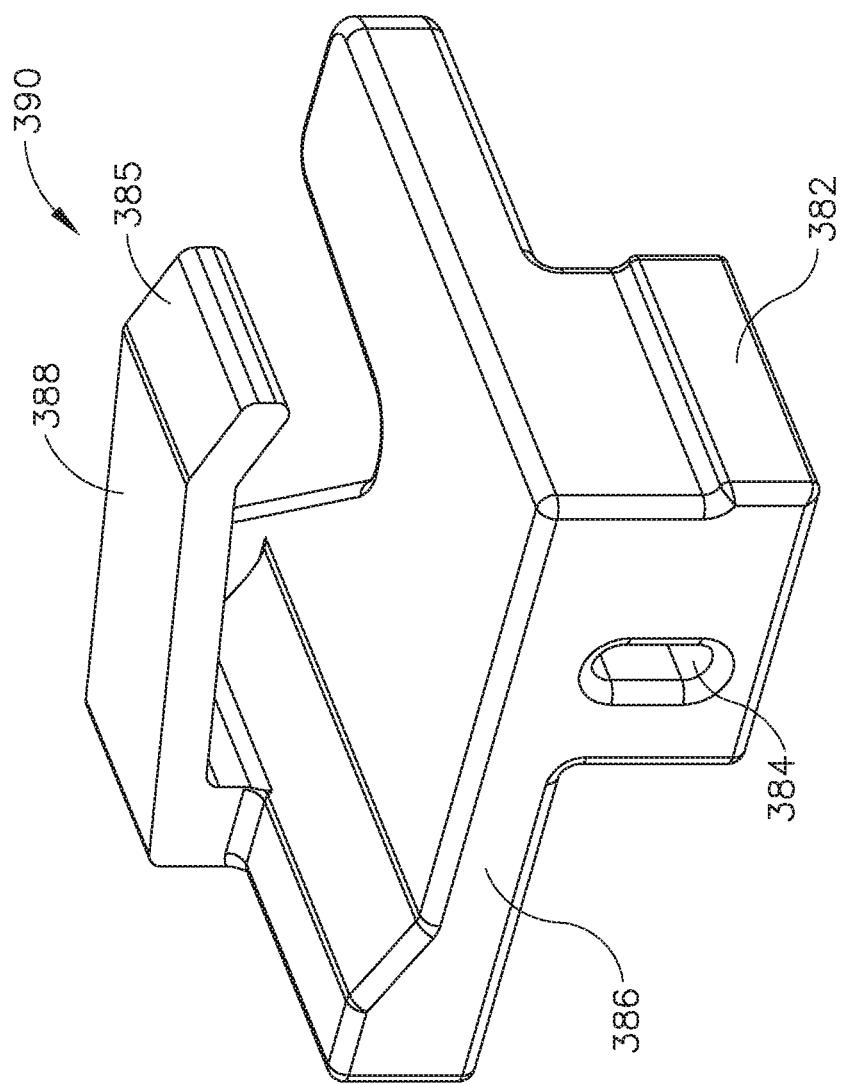

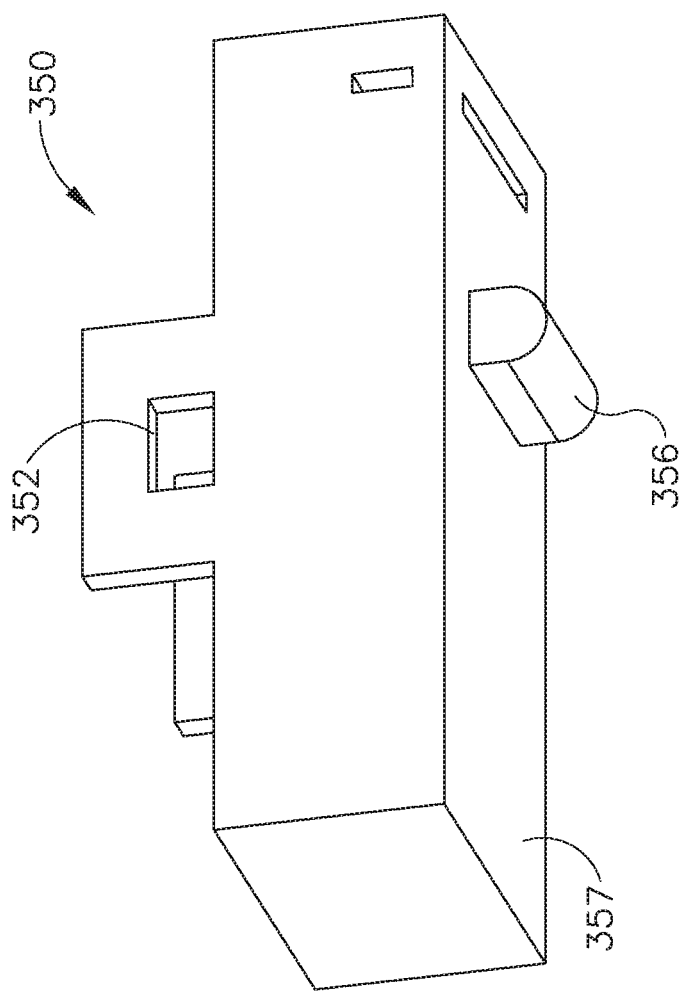

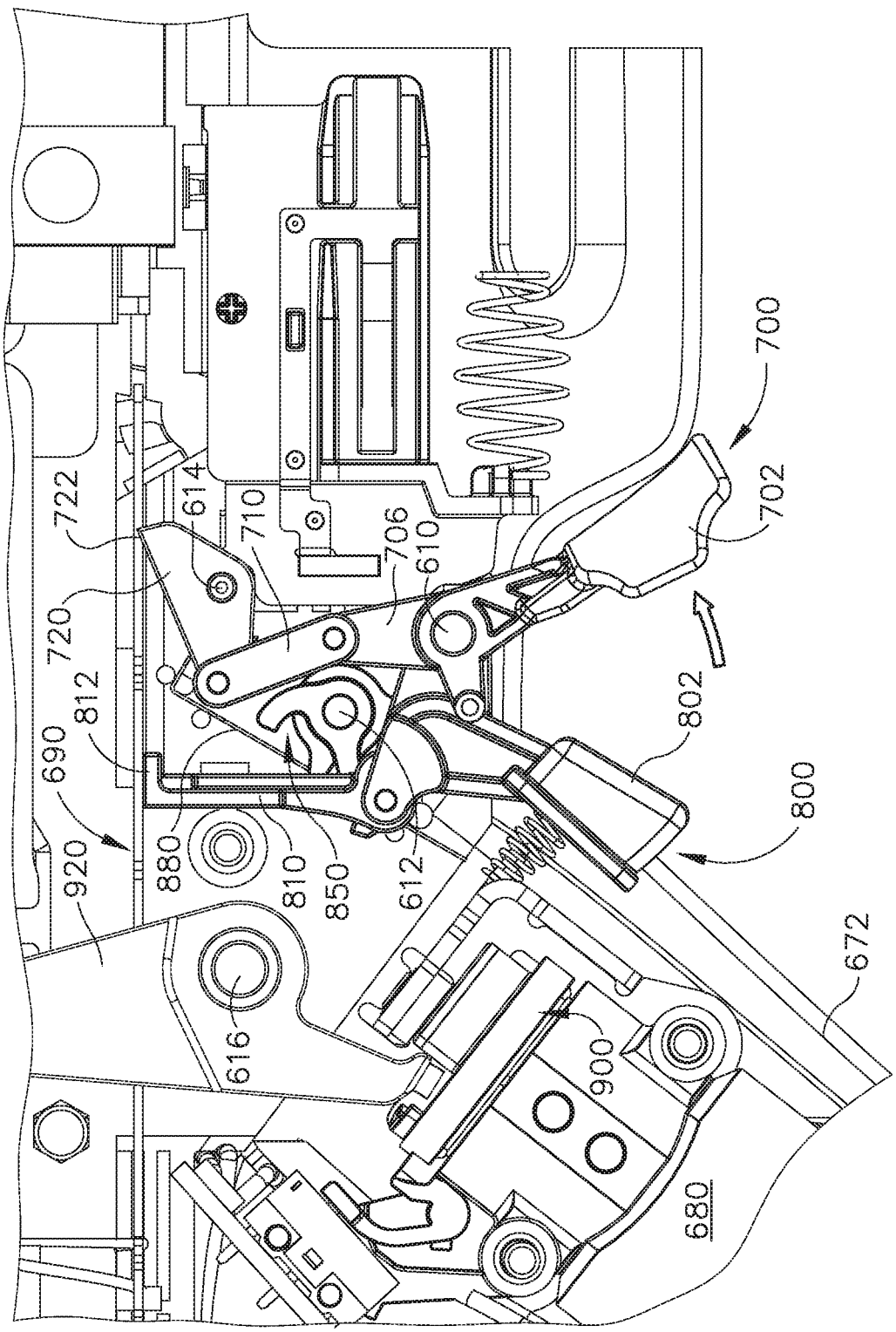

CONTROL FEATURES FOR MOTORIZED SURGICAL STAPLING INSTRUMENT

This application is a continuation of U.S. patent application Ser. No. 14/033,751, entitled "Control Features For Motorized Surgical Stapling Instrument," filed Sep. 23, 2013, now U.S. Pat. No. 9,907,552, issued Mar. 6, 2018.

BACKGROUND

In some settings, a surgeon may want to position a surgical instrument through an orifice of the patient and use the instrument to adjust, position, attach, and/or otherwise interact with tissue within the patient. For instance, in some surgical procedures (e.g., colorectal, bariatric, thoracic, etc.), portions of the gastrointestinal tract and/or esophagus, etc. may be cut and removed to eliminate undesirable tissue or for other reasons. Once the desired tissue is removed, the remaining portions may need to be recoupled together in an end-to-end anastomosis. One such tool for accomplishing these anastomotic procedures is a circular stapler that is inserted through a patient's naturally occurring orifice. Some circular staplers are configured to sever tissue and staple tissue substantially simultaneously. For instance, a circular stapler may sever excess tissue that is interior to an annular array of staples at an anastomosis, to provide a substantially smooth transition between lumen sections that are joined at the anastomosis.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pub. No. 2012/0292372, entitled "Low Cost Anvil Assembly for a Circular Stapler," published Nov. 22, 2012, now U.S. Pat. No. 8,910,847 issued Dec. 16, 2014. The disclosure of each of the above-cited U.S. Patents and U.S. Patent Application Publication is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge." issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism." issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism." issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 5 depicts an enlarged partial perspective view of an exemplary indicator assembly of the surgical instrument of FIG. 1 showing an indicator window and indicator lever;

FIG. 6 depicts an diagrammatic view of the indicator window of FIG. 5 showing an exemplary indicator bar and exemplary corresponding staple representations;

FIG. 11 depicts a top, perspective view of the shuttle of the control system of FIG. 7;

FIG. 12 depicts a bottom, perspective view of the switch enclosure of the control system of FIG. 7;

FIG. 23B depicts a perspective view of the safety trigger assembly of FIG. 19 and the firing trigger assembly of FIG. 20, with the safety trigger in an unblocking position and the firing trigger assembly in an unfired state;

Figure 1:
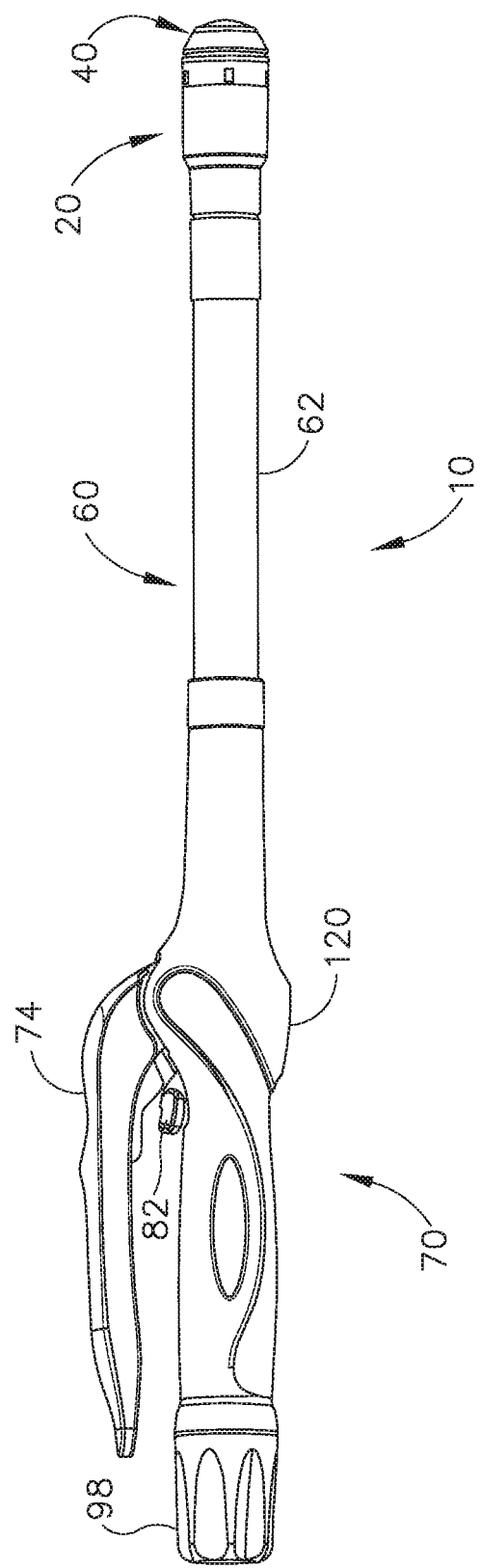
FIG. 1 depicts a side elevation view of an exemplary circular stapling surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving features (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 2A:
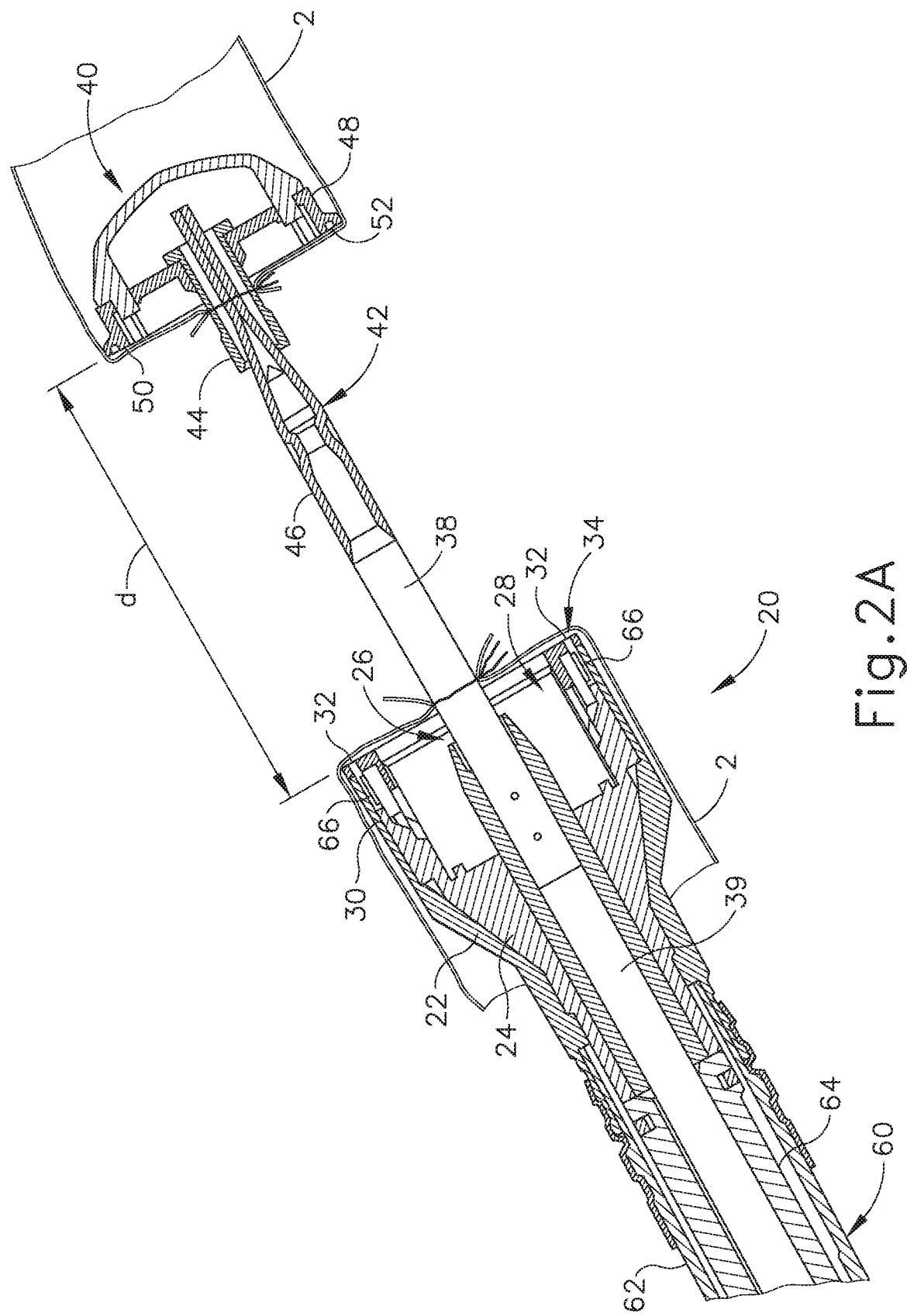
FIG. 2A depicts an enlarged longitudinal cross-section view of an exemplary stapling head assembly of the instrument of FIG. 1 showing an exemplary anvil in an open position.
Figure 2B:
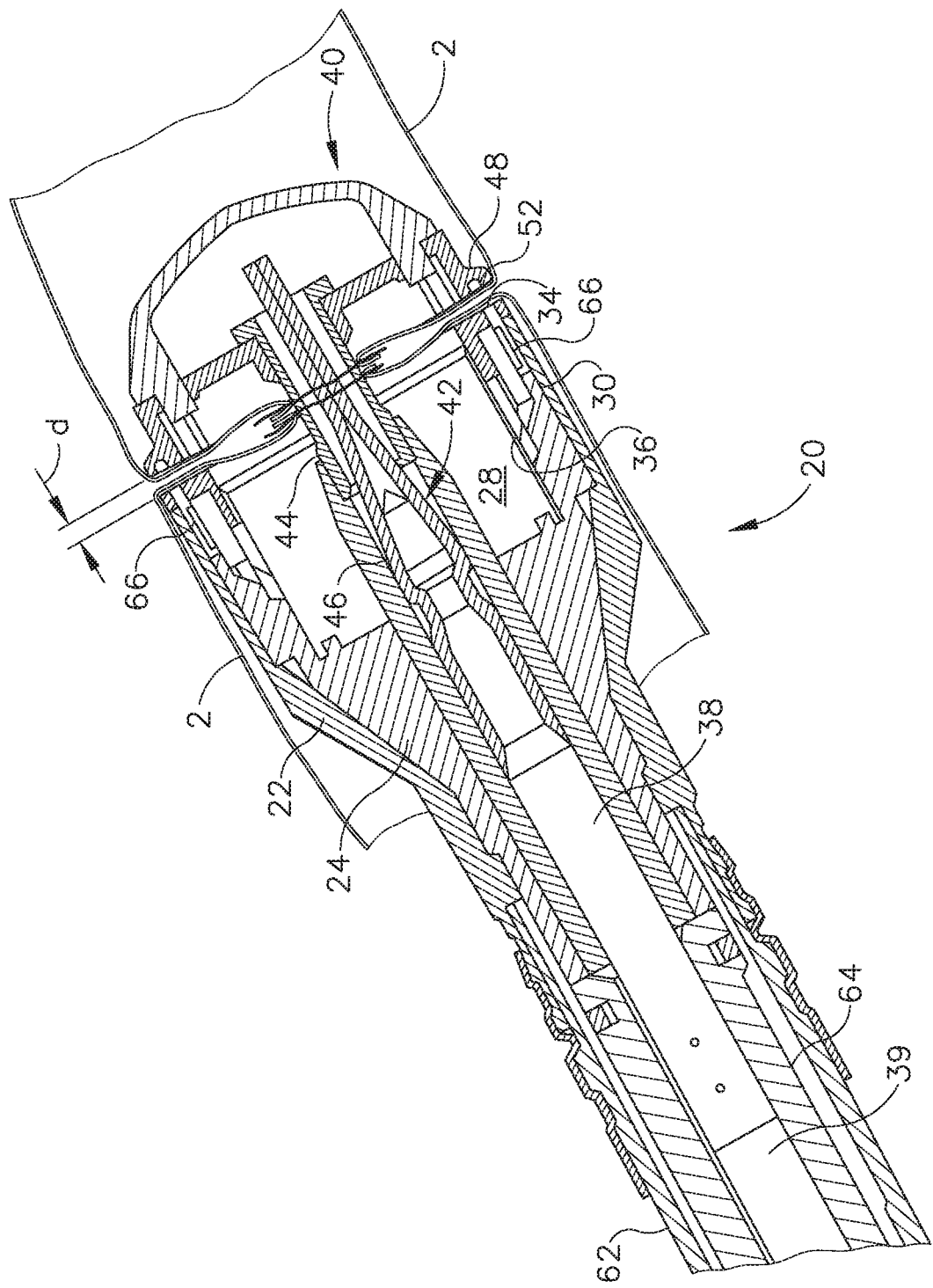
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjustment knob (98) located at a proximal end of actuator handle assembly (70), as will be described in greater detail below. Accordingly, when anvil (40) is coupled to trocar (38), rotation of adjustment knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjustment knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjustment knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, the disclosures of which are incorporated by reference herein; and/or in accordance with other configurations as will be apparent to one of ordinary skill in the art in view of the teachings herein.

D. Exemplary Actuator Handle Assembly

Figure 4A:
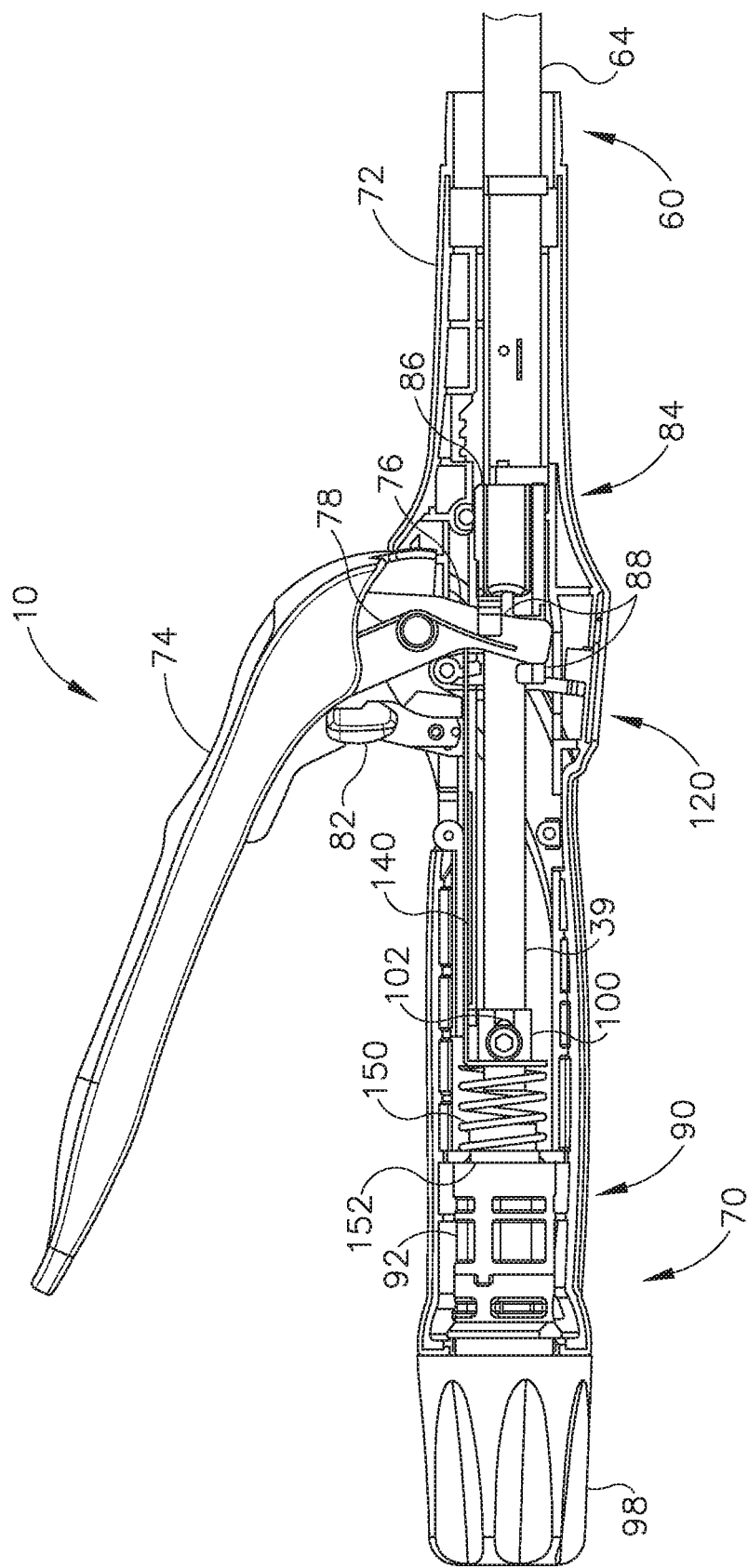
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
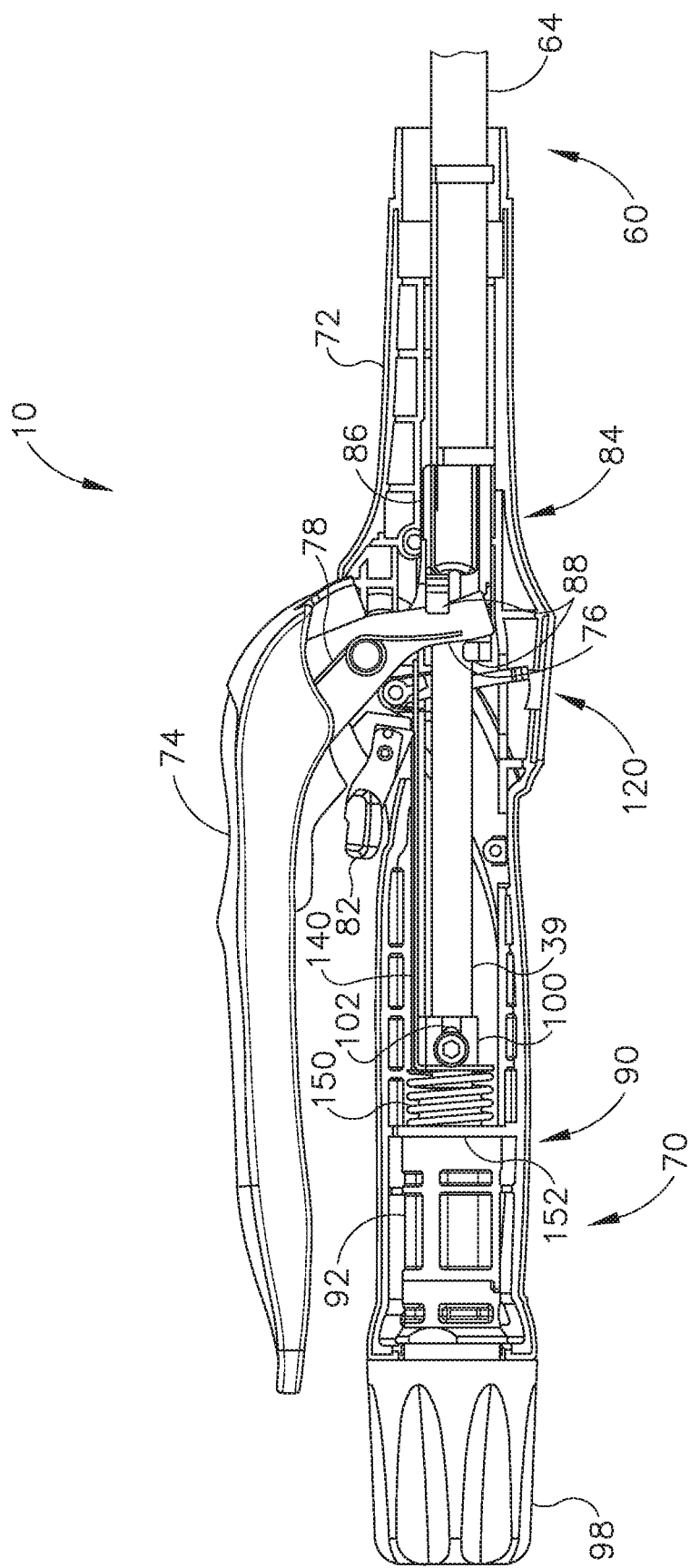
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82)

is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjustment knob (98). As best shown in FIGS. 4A-5, trocar actuation assembly (90) of the present example comprises adjustment knob (98), a grooved shank (94), and a sleeve (92). Grooved shank (94) of the present example is located at a proximal end of trocar actuator (39), though it should be understood that grooved shank (94) and trocar actuator (39) may alternatively be separate components that engage to transmit longitudinal movement. While grooved shank (94) is configured to translate within body (72), grooved shank (94) does not rotate within body (72). Adjustment knob (98) is rotatably supported by the proximal end of body (72) and is operable to rotate sleeve (92), which is engaged with grooved shank (94) via an internal tab (not shown). Adjustment knob (98) also defines internal threading (not shown) as will be described in greater detail below. Grooved shank (94) of the present example comprises a continuous groove (96) formed in the outer surface of grooved shank (94). Accordingly, when adjustment knob (98) is rotated, the internal tab of sleeve (92) rides within groove (96) and grooved shank (94) is longitudinally actuated relative to sleeve (92). Since grooved shank (94) is located at the proximal end of trocar actuator (39), rotating adjustment knob (98) in a first direction advances trocar actuator (39) distally relative to actuator handle assembly (70). Accordingly, the gap distance d between anvil (40) and stapling head assembly (20) is increased. By rotating adjustment knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial length of grooved shank (94). Middle portion (96B) comprises a section with comparably coarser pitch or fewer grooves per axial length such that relatively few rotations are required for the internal tab of sleeve (92) to traverse a long axial distance. When anvil (40) is in an initial, distal position in relation to stapling head assembly (20), the internal tab of sleeve (92) is positioned in middle portion (96B). Accordingly, the gap distance d may be quickly reduced through relatively few rotations of adjustment knob (98) while the internal tab of sleeve (92) traverses middle portion (96B). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is engaged by the internal threading defined by knob (98) when anvil (40) is substantially near to stapling head assembly (20), such that indicator bar (110) moves within indicator window (120) along scale (130) to indicate that the anvil gap is within a desired operating range, as will be described in more detail below. Accordingly, when grooved shank (94) reaches a proximal position where the proximal portion (96C) of groove (96) engages the internal threading of knob (98), each rotation of adjustment knob (98) may reduce the gap distance d by a relatively small amount to provide for fine tuning. It should be understood that the internal tab of sleeve (92) may be disengaged from groove (96) when proximal portion (96C) is engaged with the internal threading of knob (98).

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). In the present example, an extension of trocar actuator (39) engages a slot in the housing of handle assembly (70) to prevent trocar actuator (39) from rotating about its axis when adjustment knob (98) is rotated. U-shaped clip (100) of the present example further includes an elongated slot (102) on each of its opposite sides for receiving an attachment member, such as a screw, bolt, pin, etc., to selectively adjust the longitudinal position of elongated slot (102) of U-shaped clip (100) relative to trocar actuator (39) for purposes of calibrating indicator bar (110) relative to scale (130). In some versions, the attachment member (e.g., screw, bolt, pin, etc.) engages with a portion of body (72) to substantially prevent trocar actuator (39) from rotating about its axis when adjustment knob (98) is rotated.

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, the disclosures of which are incorporated by reference herein; and/or in accordance with other configurations as will be apparent to one of ordinary skill in the art in view of the teachings herein.

II. Exemplary Motorized Circular Stapler

In some instances, it may be desirable to drive staples (66) and knife (36) in a way that avoids manually driving circular surgical stapling instrument (10). For instance, in the event that the operator has inadequate hand strength to actuate circular surgical stapling instrument (10), it may be desirable to provide a motorized assembly for staple driver (24) and knife (36). Motorizing at least part of instrument (10) may also reduce the risk of operator error in driving staple driver (24) and knife (36). In some cases, operator error with a manually driven instrument (10) may result in instrument (10) failing to actuate fully. This may occur when an operator fails to fully manually actuate trigger (74), which may result in staples (66) not fully forming and thus not fully securing an anastomosis. Thus, motorizing the driving of staple driver (24) and knife (36) may ensure that knife (36) is fully driven to cut tissue, and that staples (66) are fully deployed to fasten tissue, in a single drive stroke and without interruption. It may also be desirable to prevent an operator from re-actuating circular surgical stapling instrument (10) after having already fully actuated circular surgical stapling instrument (10), in the event that circular surgical stapling instrument (10) is intended to be a single-use device used in only one single actuation.

However, it may not necessarily be desirable to motorize all portions of circular surgical stapling instrument (10). For instance, it may be desirable to maintain manual adjustment of knob (98) or a similar feature to control the distance d between anvil (40) and stapling head assembly (20). Other suitable portions of circular surgical stapling instrument (10) may also rely on manual actuation despite motorization of other features, as will be apparent to one of ordinary skill in the art in view of the teachings herein.

A. Overview

Figure 7:
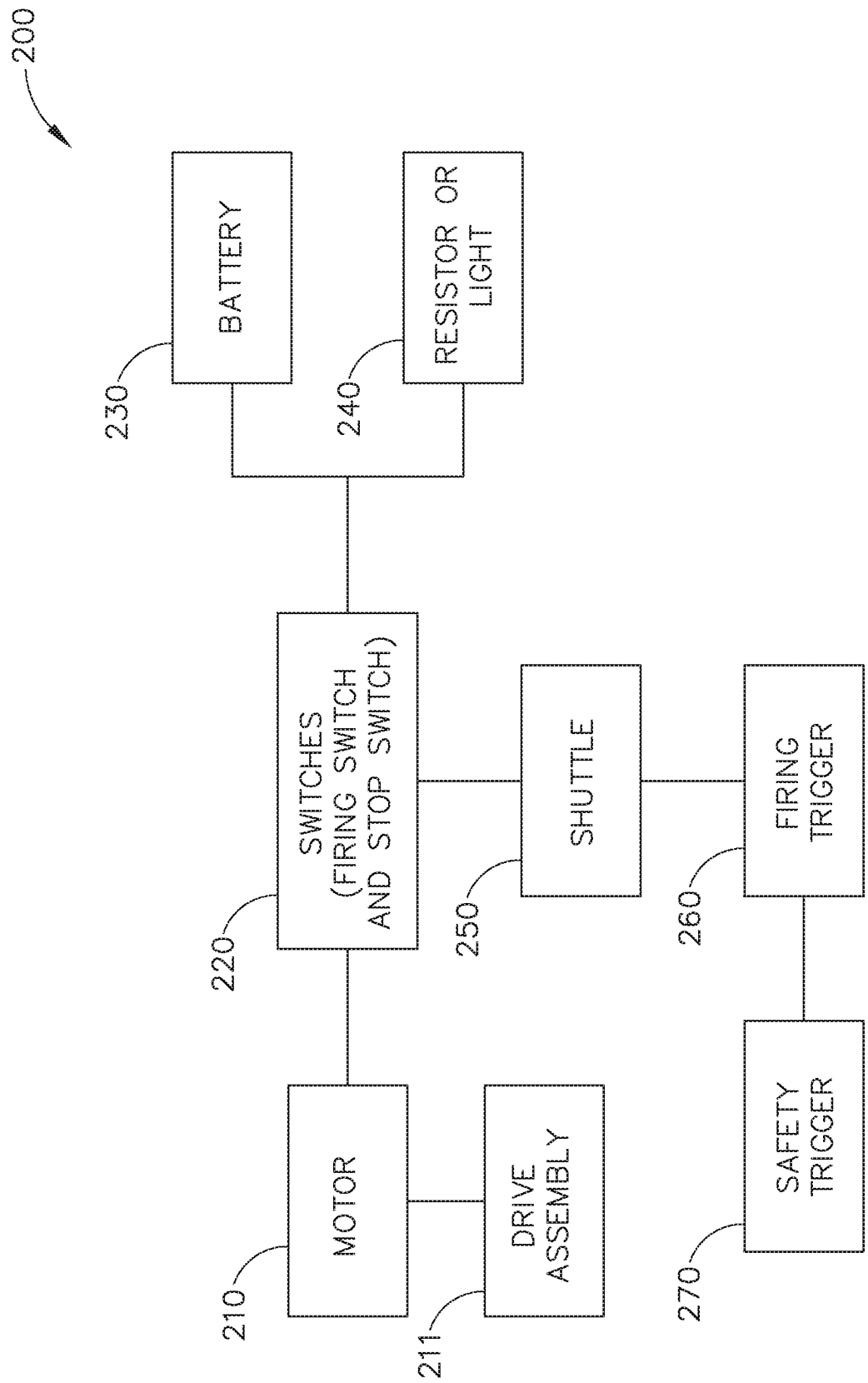
FIG. 7 depicts a schematic view of an exemplary control system for incorporation into the circular stapling surgical instrument of FIG. 1.

FIG. 7 depicts an exemplary control system (200) operable to control the actuation of a motorized version of circular surgical stapling instrument (10). As will be described in further detail below, control system (200) is operable to ensure that circular surgical stapling instrument (10) completes a full firing stroke. Control system (200) is also operable to prevent surgical stapling instrument (10) from being actuated more than once. It should be understood that that control system (200) may be integrated into handle assembly (70) of circular surgical stapling instrument (10) and may be operable to driver actuator (64) and knife (36). Control system (200) is thus operable to control cutting of tissue with knife (36) and fastening of tissue with staples (66).

Control system (200) of the present example comprises a motor (210), a plurality of switches (220), a battery (230), a power sink (240), a shuttle (250), a firing trigger (260), and a safety trigger (270). Motor (210) is operable to cause actuation of circular surgical stapling instrument (10). In particular, motor (210) is in communication with a drive assembly (211), which is operable to drive driver actuator (64) and knife (36). Motor (210) provides powered rotation to drive assembly (211), and drive assembly (211) is configured to convert such rotational motion into translational motion to translate driver actuator (64) distally and proximally as described above. Drive assembly (211) may include a rack and pinion assembly operable to translate driver actuator (64), a plurality of toggle links operable to translate driver actuator (64), one or more cams and cam followers operable to translate driver actuator (64), and/or any other suitable structures as would be apparent to one of ordinary skill in the art in view of the teachings herein. By way of example only, drive assembly (211) and/or driver actuator (64) may be configured in accordance with at least some of the teachings of U.S. patent application Ser. No. 14/033,688, entitled "Surgical Stapler with Rotary Cam Drive and Return," filed Sep. 23, 2013, published as U.S. Pub. No. 2015/0083772 on Mar. 26, 2015, now abandoned, the disclosure of which is incorporated by reference herein; U.S. patent application Ser. No. 14/033,709, entitled "Surgical Stapling Instrument with Drive Assembly Having Toggle Features," filed Sep. 23, 2013, published as U.S. Pub. No. 2015/0083773 on Mar. 26, 2015, issued as U.S. Pat. No. 9,936,949 on apr. 10, 2018, the disclosure of which is incorporated by reference herein; U.S. patent application Ser. No. 14/033,763, entitled "Surgical Stapler with Rotary Cam Drive," filed on even date Sep. 23, 2013, now U.S. Pat. No. 9,713,469, issued Jul. 25, 2017, the disclosure of which is incorporated by reference herein. Various other suitable configurations for drive assembly (211) and driver actuator (64) will be apparent to those of ordinary skill in the art in view of the teachings herein.

Motor (210) is further in communication with switches (220), which are operable to selectively couple motor (210) with battery (230). Battery (230) is operable to power motor (210). While the present example includes a battery (230), any other suitable power source may be used as would be apparent to one of ordinary skill in the art in view of the teachings herein, including but not limited to an external power source. Power sink (240) is in communication with battery (230). As will be described in greater detail below, power sink (240) is operable to discharge battery (230) (e.g., to ensure that battery (230) is fully discharged at some point after instrument (10) has been used). Power sink (240) may include a resistor, a light or bulb, which may provide the user with a visual indication (e.g., light turns off) that battery (230) has discharged; and/or any other suitable component that is operable to discharge battery (230). It should be understood that power sink (240) is merely optional.

Shuttle (250) is in communication with switches (220) and firing trigger (260). Shuttle (250) is operable to interact with firing trigger (260) such that once firing trigger (260) is depressed, a motor (210) is activated to rotate a rotary input of drive assembly (211) through a single revolution. Shuttle (250) is operable to selectively couple firing trigger (260) and switches (220) as will be described in further detail below. Safety trigger (270) is in communication with firing trigger (260) and is operable to selectively prevent the actuation of firing trigger (260).

B. Exemplary Control System

Figure 8:
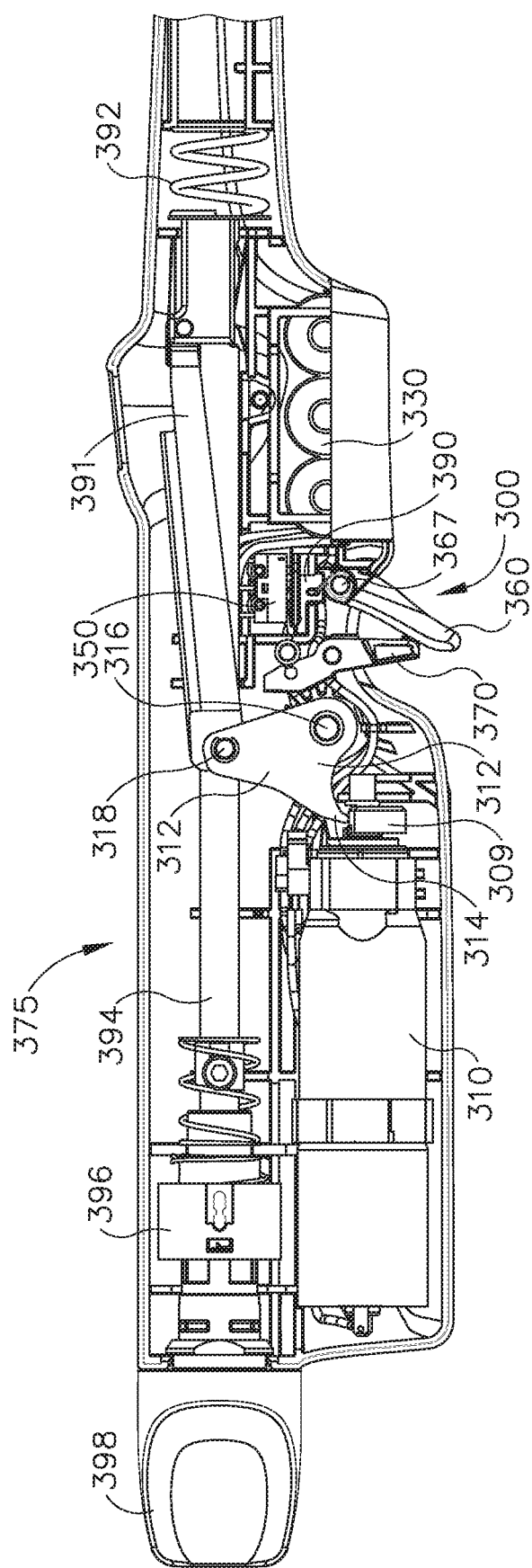
FIG. 8 depicts a side, elevation view of the interior of an exemplary hand piece incorporating the control system of FIG. 7.

FIG. 8 depicts an exemplary control system (300) integrated into a handle assembly (375). Control system (300) may be similar in functionality to control system (200) of FIG. 7, with the difference being that FIG. 7 shows a schematic view of control system (200) while FIG. 8 depicts a view of exemplary physical components embodying control system (200). It should therefore be understood that various other physical components may embody control system (200) as will be apparent to those of ordinary skill in the art in view of the teachings herein. Handle assembly (375) is substantially similar to handle assembly (70) shown in FIG. 1 with the exception of integrating control system (300) and associated components as will be discussed below. It should be understood that handle assembly (375) may be used as a substitute for handle assembly (70). Handle assembly (375) includes a rotating knob (398), which is substantially similar to rotating knob (98) of FIG. 1. Handle assembly (375) further comprises a rear linkage (396), a first internal rod (394), a second internal rod (391), internal spring (392), motor (310), safety trigger (370), firing trigger (360), battery (330), switch enclosure (350), and a shuttle (390).

Rear linkage (396) and first internal rod (394) are operable to communicate rotational motion of rotating knob (398) through handle assembly (375) to cause axial movement of anvil (40) as described above, which allows the user to selectively position anvil (40) relative to stapling head assembly (20). In particular, manual rotation of knob (398) is converted into axial movement of anvil (40) through first internal rod (394).

Figure 9:
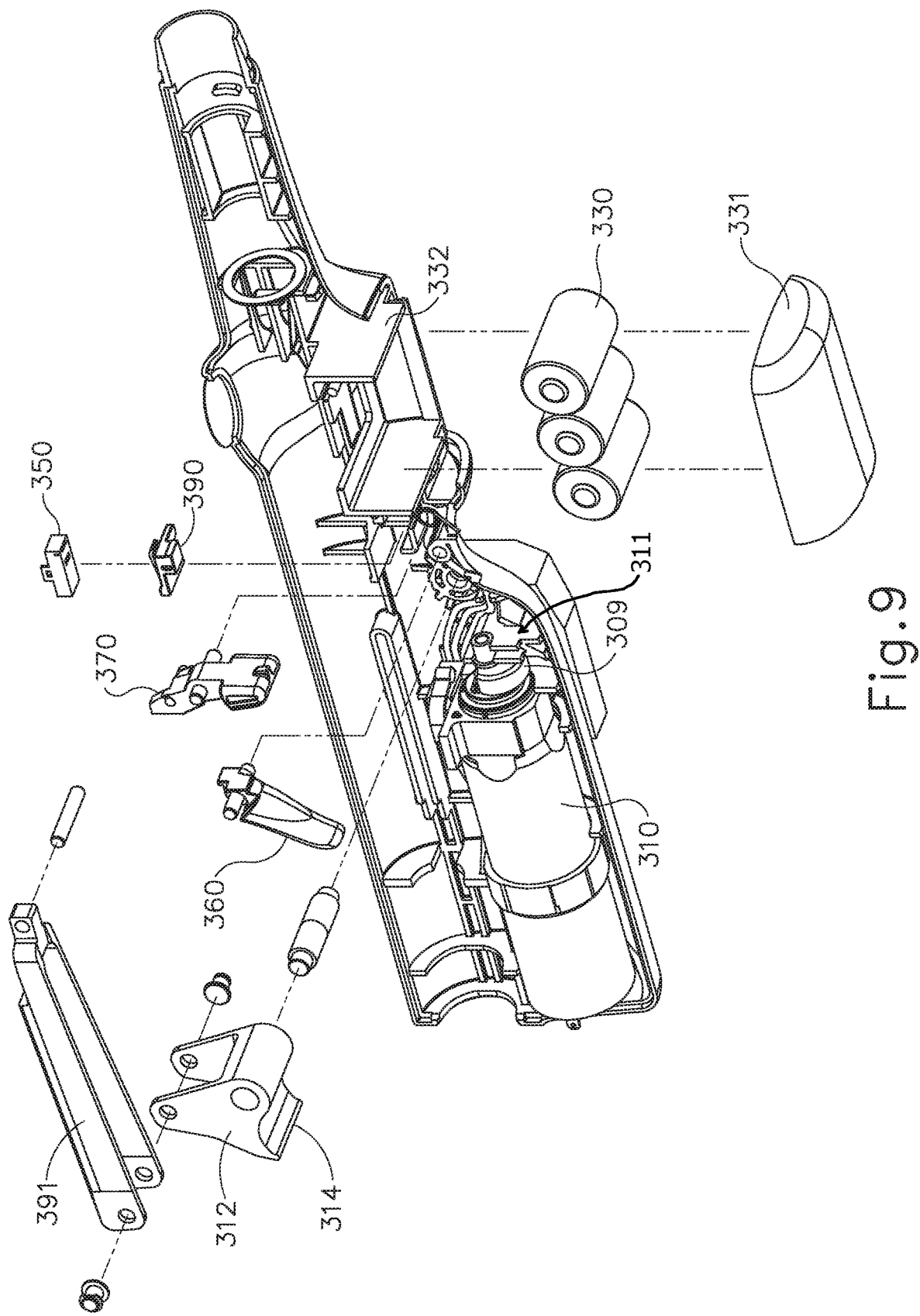
FIG. 9 depicts a bottom, exploded view of the of the control system of FIG. 7.

FIG. 9 shows an alternative view of some elements of control system (300) for incorporation into handle assembly (375) having a motor (310), drive assembly (311), firing trigger (360), switch assembly (350) battery (330), and shuttle (390). Motor (310) is shown at the proximal end of handle assembly (375) in the exemplary version, but it will be appreciated that motor (310) may be positioned in any suitable location in handle assembly (375). In some versions, motor (310) need not necessarily be located within handle assembly (375) at all. For instance, motor (310) could be positioned within a separate module and be in remote communication with handle assembly (375). Motor (310) is in communication with drive assembly (311), which is operable to convert rotational motion of motor (310) into translational motion to drive driver actuator (64) and knife (36) as described above. Drive assembly (311) comprises an eccentric cam (309), a pivoting actuator (312), and a second internal rod (391). Motor (310) rotates eccentric cam (309), which causes pivoting actuator (312) to pivot through a camming action between eccentric cam (309) and pivoting actuator (312). Pivoting actuator (312) is operable to pivot about a first pivot pin (316) and is in contact with eccentric cam (309) through a cam following edge (314). Pivoting actuator (312) further is in communication with second internal rod (391) through a second pivot pin (318), such that pivoting actuator (312) translates second internal rod (391) longitudinally when pivoting actuator (312) pivots. Second internal rod (391) is coupled with driver actuator (64) and knife (36) such that driver actuator (64) and knife (36) translate to cut and staple tissue when second internal rod (391) is advanced distally.

It should be understood that internal rod (391) will advance distally in response to rotation of motor (310). In particular, when cam (309) turns 270°, cam (309) urges pivoting actuator (312) to pivot about first pivot pin (316). This movement causes second internal rod (391) to advance distally, thereby causing driver actuator (64) and knife (36) to also advance. As cam (309) turns another 90°, cam (309) no longer urges pivoting actuator (312) to pivot about first pivot pin (316). An internal spring (392) proximally biases second internal rod (391), thereby causing driver actuator (64) and knife (36) to proximally retract. In some other versions, a feature of cam (309) actively retracts driver actuator (64) and knife (36) in accordance with one or more of the teachings of U.S. patent application Ser. No. 14/033, 688, entitled SURGICAL STAPLER WITH ROTARY CAM DRIVE AND RETURN, filed Sep. 23, 2013, published as U.S. Pub. No. 2015/0083772 on Mar. 26, 2015, now abandoned, the disclosure of which is incorporated by reference herein. In the present example, cam (309) is configured to provide clearance for proximal pivoting of pivoting actuator (312) (and, hence, proximal retraction of second internal rod (391), etc.) as cam (309) completes the second 180 degrees of rotation. Once cam (309) has traversed the full 360° of rotation, second internal rod (391) has translated from a proximal-most position to a distal-most position and then back to the proximal-most position. Thus, driver actuator (64) and knife (36) fire and retract with a single revolution of cam (309). While the full 360° revolution of cam (309) is allocated as 270° for distal motion of driver actuator (64) and the remaining 90° for proximal motion of driver actuator, it should be understood that the allocation may be made in any other suitable fashion (e.g., 180° for distal motion and 180° for proximal motion, etc.). It should also be understood that a full range of distal and proximal travel may be provided by less than 360° of rotation of cam (309).

Batteries (330) are in selective communication with motor (310) as will be described in further detail below. Batteries (330) in the present example comprise a set of three batteries stored in a casing (331) that clips into compartment (332). Of course, any other suitable number of batteries (330) may be used. In some versions, an external power source or different power source may be used in addition to or in lieu of batteries (330) as would be apparent to one of ordinary skill in the art in view of the teachings herein.

Figure 10:
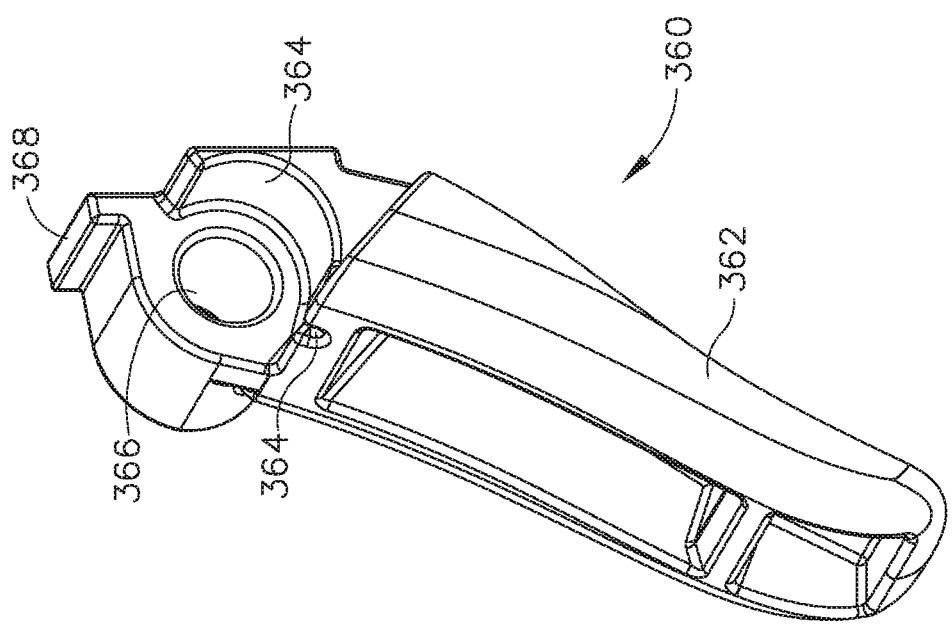
FIG. 10 depicts a top, perspective view of the firing trigger of the control system of FIG. 7.
Figure 13A:
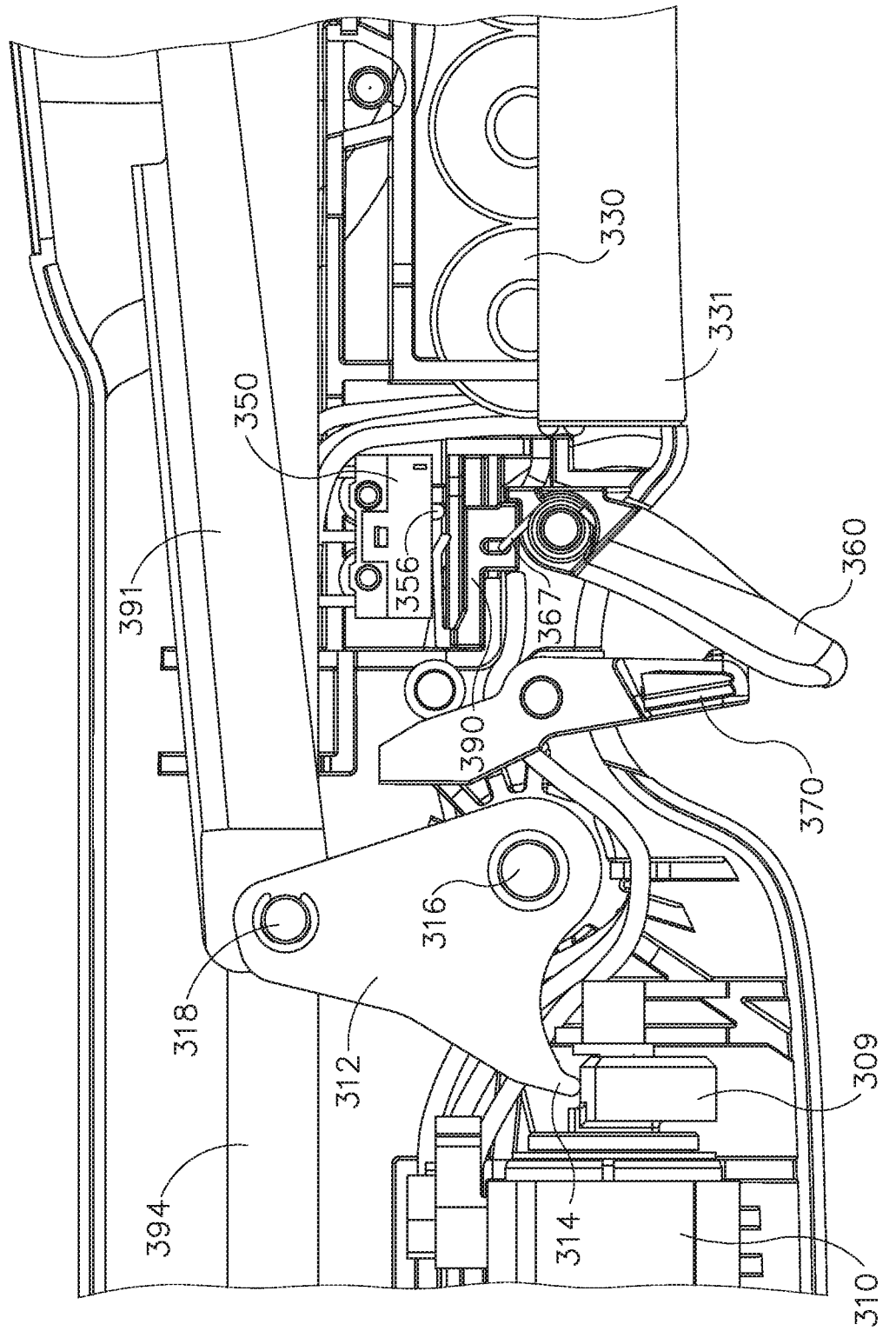
FIG. 13A depicts a side, enlarged view of the handpiece of FIG. 8 showing the firing trigger in an unactivated state.
Figure 13B:
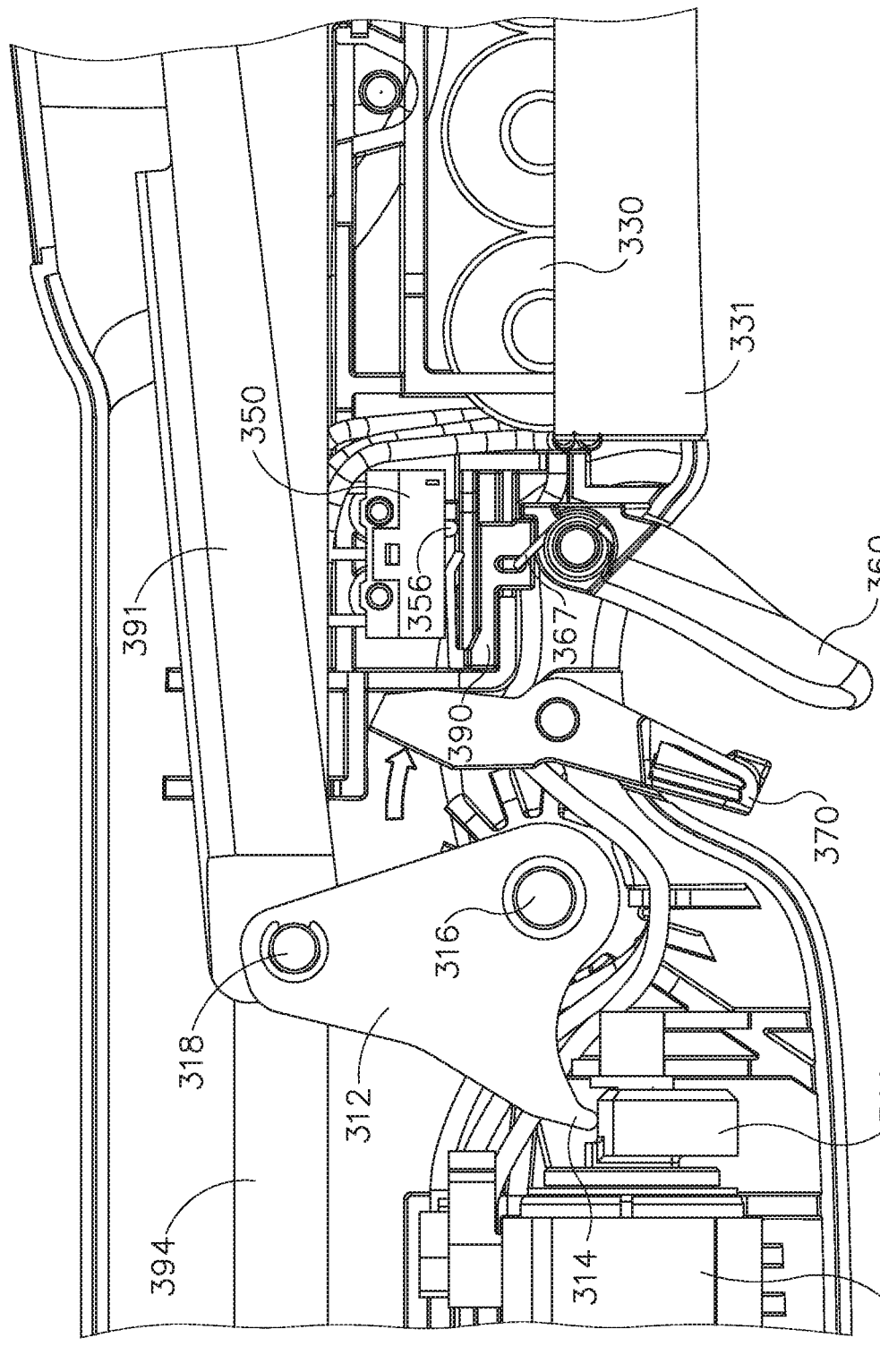
FIG. 13B depicts a side, enlarged view of the handpiece of FIG. 8 showing the safety trigger released and the firing trigger in an unactivated state.
Figure 13C:
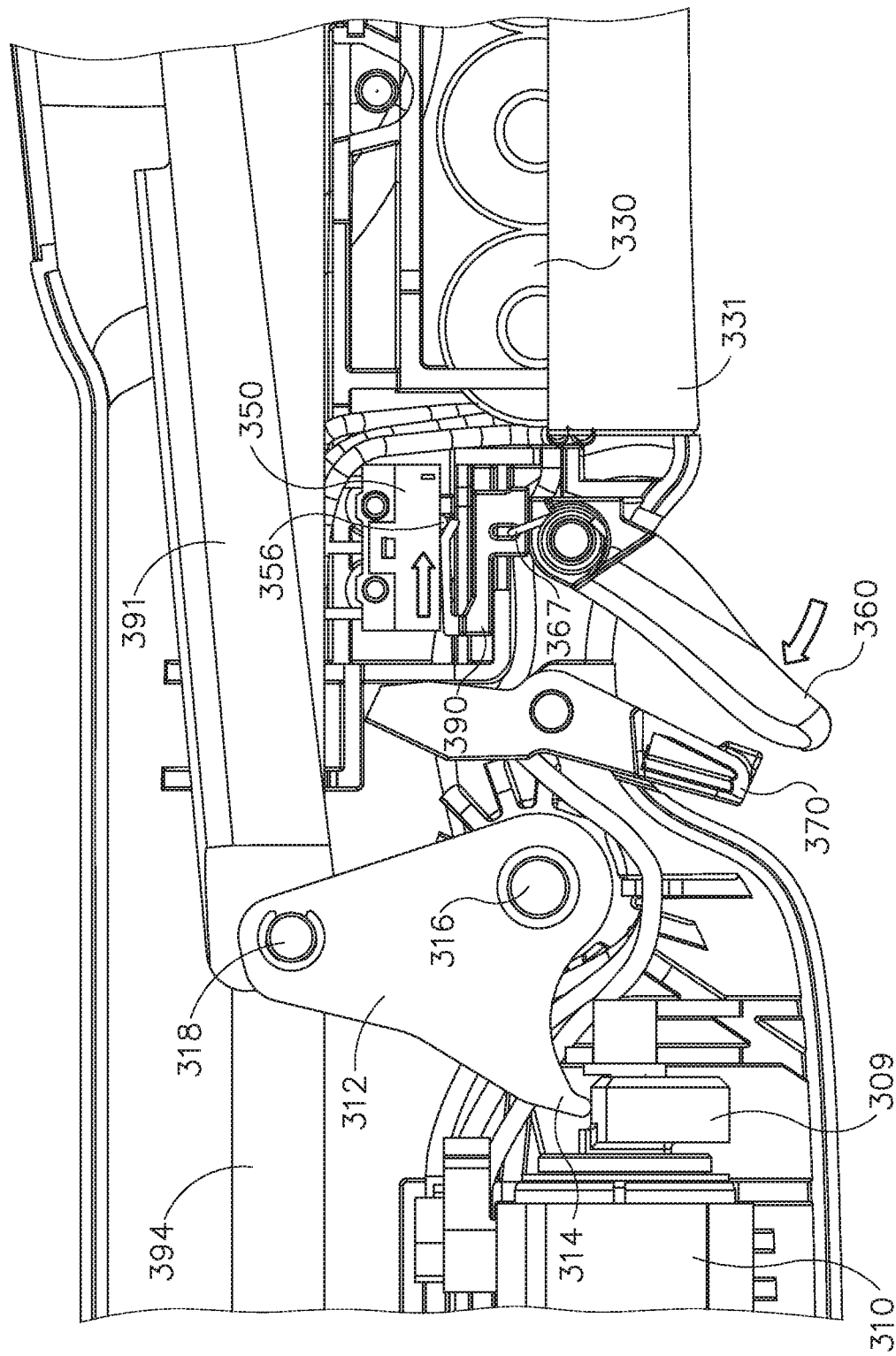
FIG. 13C depicts a side, enlarged view of the handpiece of FIG. 8 showing the firing trigger in an activated state and a shuttle advanced.

FIG. 10 shows firing trigger (360) in greater detail. Firing trigger (360) comprises an engagement portion (362) configured to be engaged by the finger of an operator. Engagement portion (362) may be pulled proximally by the operator to actuate firing trigger (360). Firing trigger (360) further defines a spring groove (364), a pin hole (366), and a shuttle stop (368). As shown in FIGS. 13A-13C, the first end of a torsion spring (367) fits in spring groove (364). Torsion spring (367) further engages shuttle (390) as will be described in greater detail below. A pin is placed through pin hole (366) such that firing trigger (360) pivots about the axis defined by pin hole (366). Shuttle stop (368) is in the form of an integral protrusion extending upwardly from firing trigger (360). Shuttle stop (368) is positioned to engage shuttle (390) such that shuttle (390) holds firing trigger (360) in a pivoted position after firing trigger (360) has pivoted. As will be described in greater detail below, when the operator pivots trigger (360) in a first direction, torsion spring (367) advances shuttle (390) distally, and the distally advanced shuttle (390) cooperates with shuttle stop (368) to prevent trigger (360) from pivoting back in a second direction. Trigger (360) is thus effectively locked at the pivoted position after trigger (360) has been pivoted in the first direction.

FIG. 11 shows shuttle (390) in greater detail. Shuttle (390) comprises a body portion (386) that is slidably disposed in handle assembly (375). Body portion (386) defines a slot (384) that receives a second end of torsion spring (367). The coupling of shuttle (390) with trigger (360) via torsion spring (367) will cause shuttle (390) to advance distally when trigger (360) is pivoted. Shuttle (390) also comprises an engagement block (382) and an arm (388). Engagement block (382) is configured to engage shuttle stop (368) of firing trigger (360) once firing trigger (360) has been pivoted as described above. Arm (388) extends obliquely upwardly from body portion (386), though it should be understood that arm (388) may have various other suitable configurations. Arm (388) defines an arm tip (385), which is operable to slide along the underside of switch enclosure (350) as will be described in greater detail below. Arm (388) is constructed of a resilient material such that arm tip (385) is resiliently biased upwardly to actuate a switch (356) on the underside of switch enclosure (350) as shuttle (390) is slid distally relative to switch enclosure (350). In the present example, trigger (360) must be fully pivoted in order for shuttle (390) to be driven distally enough to actuate switch (356). Thus, merely partial pivoting of trigger (360) will have no operative effect.

As shown in FIG. 12, switch enclosure (350) comprises tabs (352) that are configured to secure switch enclosure to handle assembly (375). Of course, switch enclosure (350) may be coupled with handle assembly (375) in any other suitable fashion. The configuration shown in FIG. 12 is not intended to be limiting in any way. Switch enclosure (350) further comprises a switch (356) that is operable to be mechanically actuated. In particular, and as noted above, arm (388) of shuttle (390) is slidable along the lower surface (357) of switch enclosure (350) such that arm tip (385) eventually actuates switch (356). This distal advancement of shuttle (390) occurs when firing trigger (360) is actuated, such that torsion spring (367) drives shuttle (390) distally relative to enclosure (350), causing arm tip (385) to actuate switch (356). Switch (356) is in communication with battery (330) and motor (310) and is movable between an activated (depressed) state and a non-activated (non-depressed) state. In the activated state, switch (356) establishes electrical communication between battery (330) and motor (310). In the non-activated state, switch (356) breaks electrical communication between battery (330) and motor (310).

In some versions, switch (356) is resiliently biased downwardly to assume the non-activated position shown in FIG. 12. As firing trigger (360) is pivoted to rotate torsion spring (367), torsion spring (367) rotates to distally advance shuttle (390) distally. As shuttle (390) advances distally, arm tip (385) triggers switch (356) by toggling switch (356) upwardly. Once arm tip (385) advances past switch (356), the downward bias of switch (356) may cause switch (356) to bear downwardly on arm tip (385). With arm tip (385) being resiliently biased upwardly, the opposing resilient biases may provide increased friction between arm (388) and switch (356), which may help maintain the distally advanced position of shuttle (390). Furthermore, once firing trigger (360) is pivoted to the pivoted position, engagement between shuttle stop (368) and engagement block (382) of shuttle (390) prevents firing trigger (360) from pivoting in the reverse direction. Tension in torsion spring (367) may further help maintain the distally advanced position of shuttle (390). Thus, once trigger (360) is pivoted from a first position (FIGS. 13A-13B) to a second position (FIG. 13C), trigger (360) is effectively locked in the second position and shuttle (390) will maintain a distally advanced position.

C. Exemplary Actuation Sequence

FIG. 13A shows control system (300) in a pre-firing state. At this stage, circular surgical stapling instrument (10) is not yet actuated and may be in the process of being positioned for use (e.g., similar to the stage shown in FIG. 2A). In the pre-firing state, safety trigger (370) is engaged such that firing trigger (360) cannot be actuated by the operator. Batteries (330) and motor (310) are not in communication. Motor (310) is not receiving any power. Safety trigger (370) mechanically blocks firing trigger (360) in the present example. In some other versions, an electronic safety or some other type of lockout feature is used. As described above in reference to FIGS. 2B and 5-6, a gap between anvil (40) and stapling head assembly (20) may be adjusted using knob (98). Safety trigger (370) is in communication with the same features driving bar (110) relative to indicator window (120) such that safety trigger (370) cannot pivot unless the range of the gap between anvil (40) and stapling head assembly (20) falls in a desired operating range (e.g., a "green zone"). While safety trigger (370) is configured to mechanically block firing trigger (360) until indicator bar (110) falls within the green zone in the present example, in some other versions safety trigger (370) may be in electrical communication with motor (310) such that motor (310) cannot be activated unless indicator bar (110) falls within the green zone. In the pre-firing state, shuttle (390) is in a proximal, pre-firing position; and switch (356) is in the non-activated state.

FIG. 13B shows safety trigger (370) being actuated such that firing trigger (360) is unblocked and ready for actuation. At this stage, anvil (40) has been suitably positioned relative to stapling head assembly (20) such that the gap distance therebetween is within the desired operating range. The operator then actuates trigger (360), as shown in FIG. 13C. Actuation of trigger (360) rotates torsion spring (367) and causes shuttle (390) to advance distally as seen in FIG. 13C as a result of torsion spring (367) distally urging shuttle (390) via coil slot (384). As shuttle (390) advances distally, arm (388) actuates switch (356). Switch (356) then establishes electrical communication between motor (310) and batteries (330). Thereafter, motor (310) rotates cam (309) through a single revolution as described above to distally advance and proximally retract driver actuator (64) and knife (36). This drives staples (66) into tissue in an annular array and causes knife (36) to sever excess tissue from within that annular array, as shown in FIG. 2C.

Once shuttle (390) has distally advanced, shuttle (390) maintains a distally advanced position, which prevents firing trigger (360) from pivoting back to the position shown in FIGS. 13A-13B due to engagement between shuttle stop (368) and engagement block (382). Shuttle (390) will also maintain the distally advanced position. Thus, once switch (356) is activated, switch (356) cannot be re-activated, and trigger (360) is effectively disabled. Furthermore, once switch (356) is activated and electrical communication is established between motor (310) and batteries (330), the activation of motor (310) cannot be interrupted or otherwise affected by further manipulation of firing trigger (360). To further ensure that only a single actuation may occur, after the first firing sequence is completed, batteries (330) may be completely discharged of remaining power by a feature like power sink (240) of FIG. 7, as will be described in greater detail below.

III. Exemplary Electrical Circuit for Motorized Circular Stapler

Figure 14:
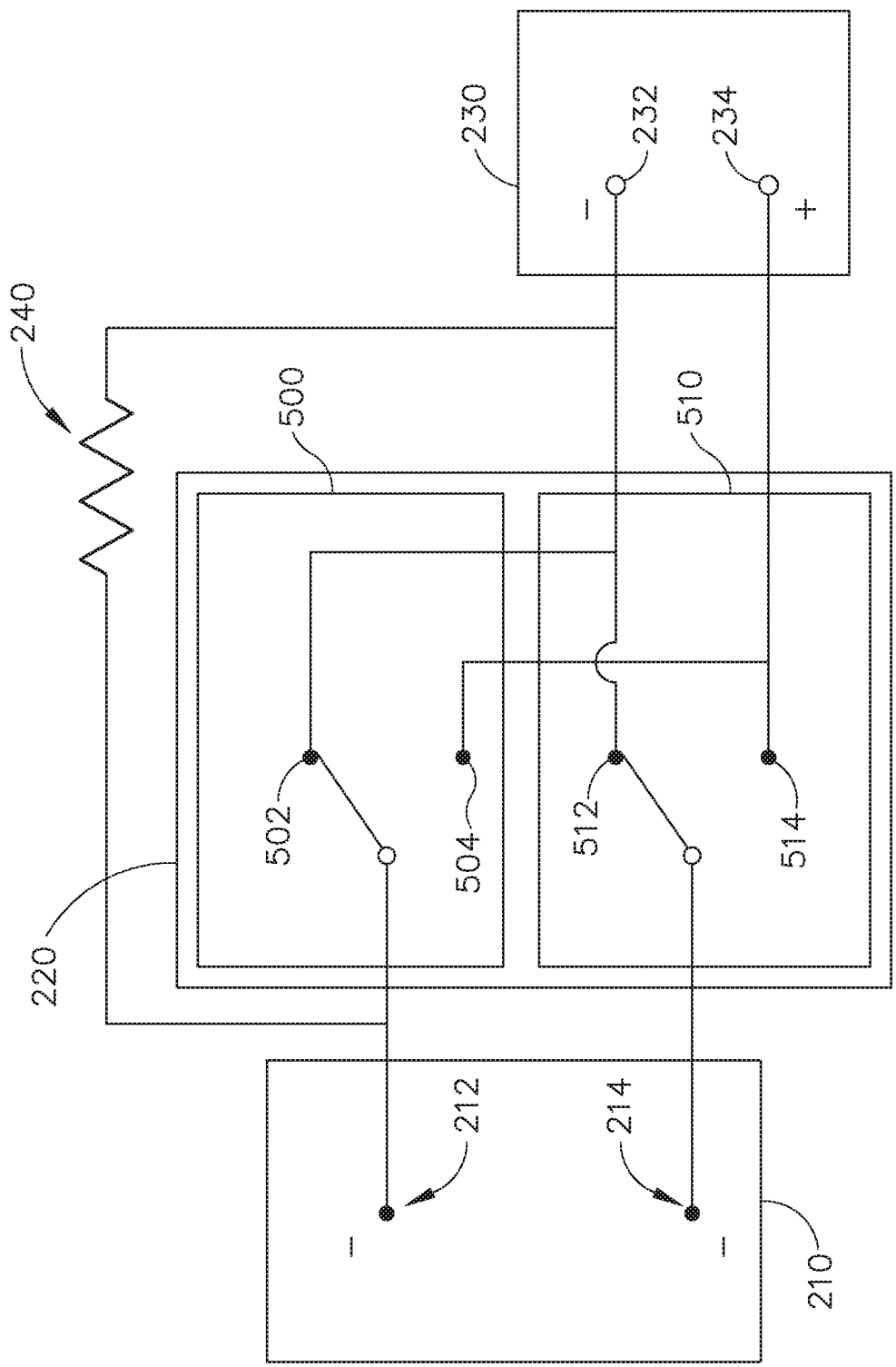
FIG. 14 depicts a schematic view of the switches of the control system of FIG. 7 in an unfired state.
Figure 15:
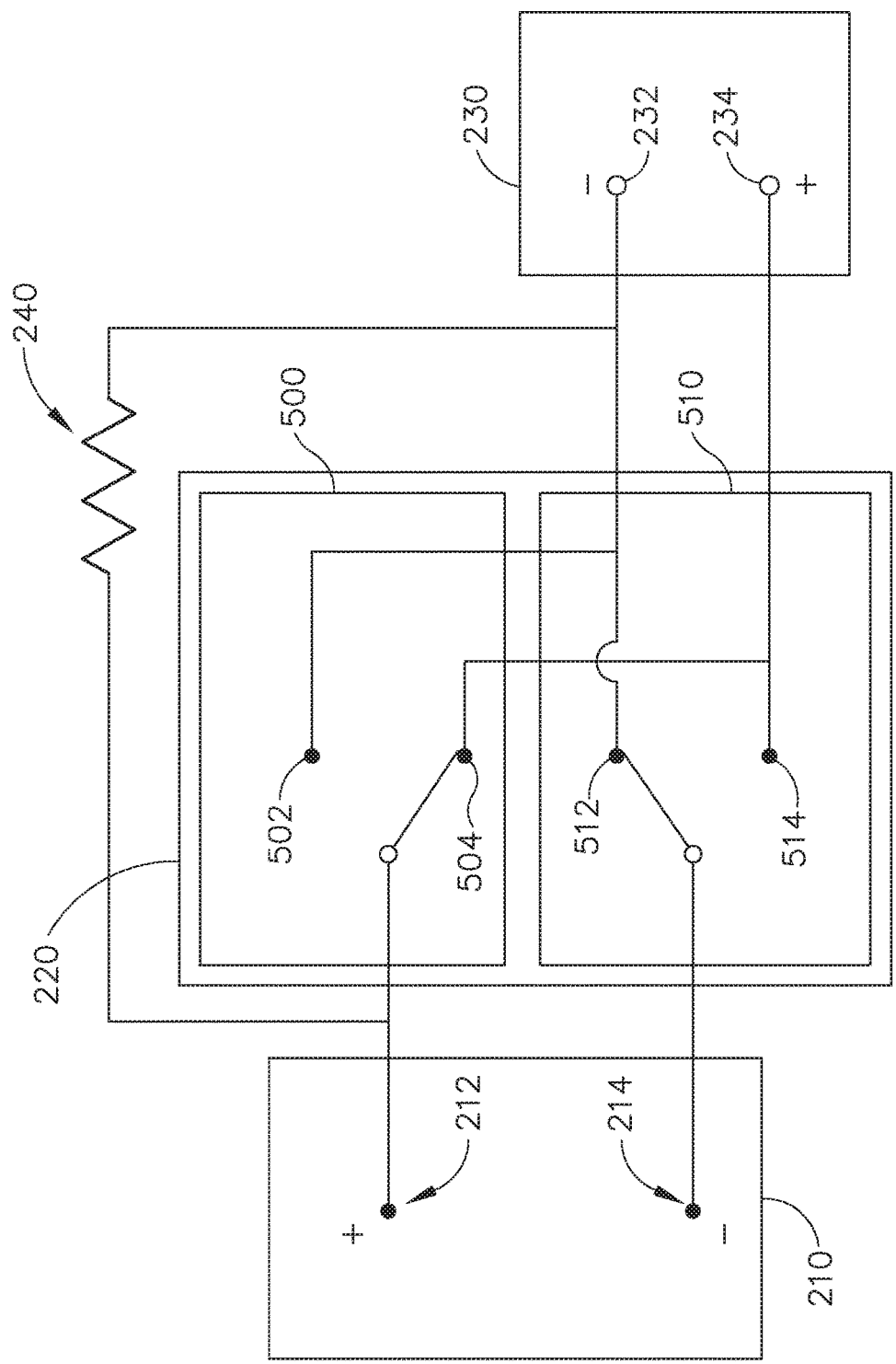
FIG. 15 depicts a schematic view of the switches of the control system of FIG. 7 in a firing state.
Figure 16:
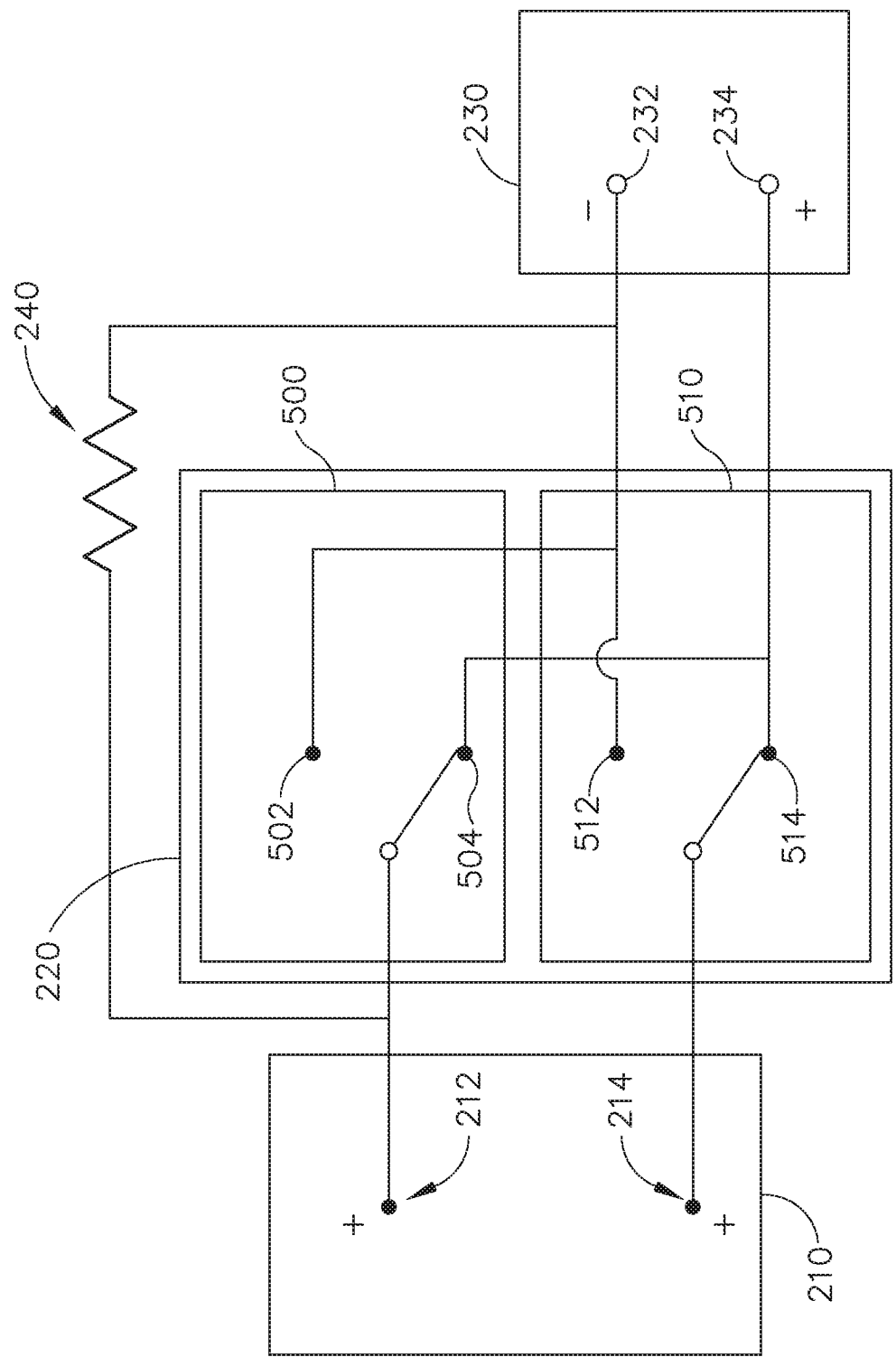
FIG. 16 depicts a schematic view of the switches of the control system of FIG. 7 in an exhausted device state.

FIGS. 14-16 show an exemplary circuit arrangement that may be incorporated into control system (200, 300). While FIGS. 14-16 use reference numbers associated with control system (200), it should be understood that the same circuit arrangement may be readily incorporated into control system (300) and/or various other control systems. As noted above, it may be desirable to have batteries (230) discharge after motor (210) has completed a drive stroke in instrument (10). The circuit arrangement shown in FIGS. 14-16 may provide such discharge of batteries (230) as will be described in greater detail below. The arrangement shown in FIGS. 14-16 will also effectively short circuit motor (210) after motor (210) has completed a drive stroke in instrument (10), further ensuring that motor (210) will not be re-activated after motor (210) has completed a drive stroke.

As shown in FIGS. 14-16, switches (220) comprise a firing switch (500) and a stop switch (510). Firing switch (500) and stop switch (510) are operable generally to control the electrical connection between motor (210) and batteries (230). Batteries (230) have a negative battery lead (232) and positive battery lead (234). Motor (210) has a first motor lead (212) and second motor lead (214). Firing switch (500) has a first contact (502) and a second contact (504). Stop switch (510) has a first contact (512) and a second contact (514). In some versions, switches (510, 512) are integrated into a single module such as switch enclosure (350). Other suitable configurations will be apparent to those of ordinary skill in the art in view of the teachings herein.

FIG. 14 shows firing switch (500) and stop switch (510) in an unfired state. In particular, first motor lead (212) is coupled with first contact (502) of firing switch (500), which establishes communication between first motor lead (212) and negative battery lead (232). Second motor lead (214) is coupled with first contact (512) of stop switch (510), which establishes communication between second motor lead (214) and negative battery lead (232). Since both motor leads (212, 214) are in communication with negative battery lead (232), batteries (230) do not power motor (210). Positive battery lead (234) is only coupled with second contacts (504, 514), which are not coupled with anything else. Thus, batteries (230) are not under any kind of load or power draw. It will be appreciated that the state of firing switch (500) and stop switch (510) shown in FIG. 14 may correspond with the operating state shown in FIG. 13A. Within the context of control system (300) of FIG. 8, such a state represents a state when firing trigger (360) has not yet been actuated.

FIG. 15 shows firing switch (500) and stop switch (510) in a firing state. By way of example only, switches (500, 510) may transition to this state when arm (388) actuates switch (356). In this state, first motor lead (212) is coupled with second contact (504) of firing switch (500), which establishes communication between first motor lead (212) and positive battery lead (234). Second motor lead (214) is coupled with first contact (512) of stop switch (510), which establishes communication between second motor lead (214) and negative battery lead (232). Since first motor lead (212) is in communication with positive battery lead (234) and second motor lead (214) is in communication with negative battery lead (232), batteries (230) provide power to motor (210) and thereby activate motor (210). Motor (210) thus actuates the drive assembly (211) to drive driver actuator (64) and knife (36) as described above. It will be appreciated that the state of firing switch (500) and stop switch (510) may correspond generally to the state shown in FIG. 13C when circular surgical stapling instrument (10) is fired. Within the context of control system (300) of FIG. 8, such firing involves the user disengaging safety trigger (370) and actuating firing trigger (360).

FIG. 16 shows firing switch (500) and stop switch (510) in an exhausted state. In this state, first motor lead (212) is coupled with second contact (504) of firing switch (500), which establishes communication between first motor lead (212) and positive battery lead (234). Second motor lead (214) is coupled with second contact (514) of stop switch (510), which establishes communication between second motor lead (214) and positive battery lead (234). Since both motor leads (212, 214) are in communication with positive battery lead (234), batteries (230) do not power motor (210); and a short circuit is provided between first motor lead (212) and second motor lead (214). This short circuit prevents motor (210) from receiving power and effectively de-activates motor (210). In the present example, the short-circuiting of motor (210) will dynamically brake motor (210), though it should be understood that motor (210) may be stopped in any other suitable fashion. By way of example only, in some instances, software, a microcontroller, microprocessor, ASIC, and/or other type of control module is in communication with battery (230) and motor (210) and is configured to automatically stop motor (210) thereby providing a way to dynamically brake motor (210) such that motor (210) may be actuated for exactly one drive stroke of drive assembly (211). By way of example only, such a control module may be in communication with an encoder and/or one or more reed switches that are in communication with one or more components of drive assembly (211). Other suitable types of sensors and control modules that may be used to provide precise stopping of motor (210) (e.g., based on tracked positioning of one or more components of drive assembly (211), etc.) will be apparent to those of ordinary skill in the art in view of the teachings herein. Of course, a control module may be configured to control motor (210) to activate for any suitable number of rotations, etc.

Within the context of control system (300) of FIG. 8, it will be understood that stop switch (510) may be actuated in response to motor (310) driving cam (309) through a single revolution, which would represent a single actuation of circular surgical stapling instrument (10). The completion of such a single revolution may be detected and communicated to switches (220) in various ways. By way of example only, an encoder wheel and sensor, optical sensor, and/or other type of sensor may be in communication with motor (310) and/or other rotating components such that the sensor is operable to track the rotation. As another merely illustrative example, one or more reed switches and/or other types of sensors may be configured and positioned to track translation of second internal rod (391), which may be indicative of cam (309) rotation. Yet another merely illustrative example is described below with reference to FIGS. 28A-28B. Other suitable ways in which switches (220) may be automatically transitioned from the firing state (FIG. 15) to the exhausted state (FIG. 16) upon completion of a full revolution of cam (309) will be apparent to those of ordinary skill in the art in view of the teachings herein.

Also in the exhausted state shown in FIG. 16, battery leads (232, 234) are coupled with power sink (240). In some versions, power sink (240) is incorporated into a battery pack with batteries (230). Power sink (240) eventually drains the power from batteries (230). In some instances, battery leads (232, 234) are coupled with power sink (240) as soon as a battery pack containing batteries (230) is coupled with handle assembly (375). Power sink (240) may thus begin discharging batteries (230) before motor (210) is even first activated. In some other instances, battery leads (232, 234) are coupled with power sink (240) in response to actuation of a stop switch actuator (962) at the end of a firing stroke, as will be described in greater detail below.

IV. Exemplary Alternative Motorized Circular Stapler

A. Overview

Figure 17:
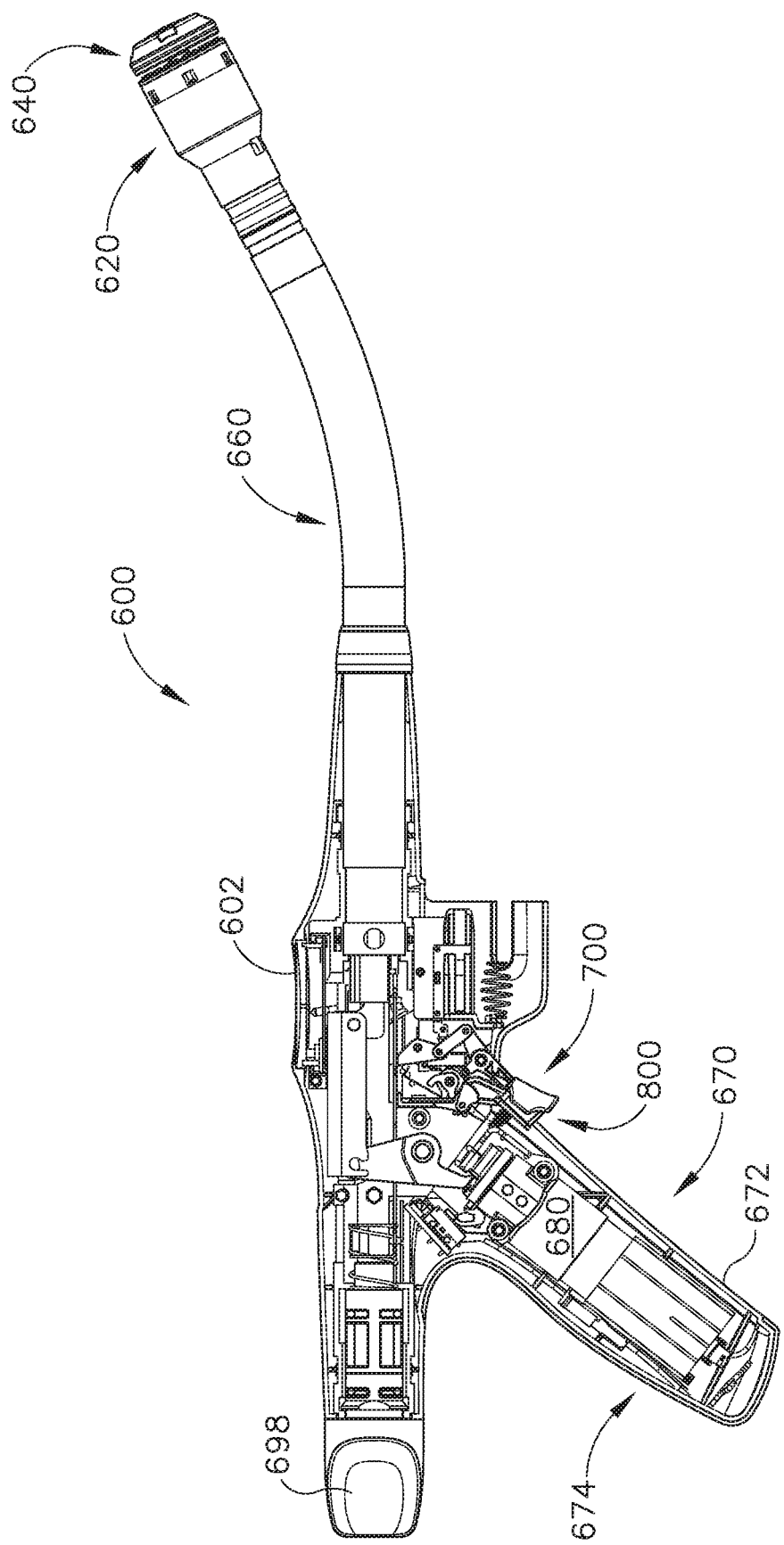
FIG. 17 depicts a side elevation view of an exemplary circular stapling surgical instrument, with a housing half and battery pack removed.

FIG. 17 shows an exemplary alternative motorized stapling instrument (600). Instrument (600) of this example includes a stapling head assembly (620), a curved shaft assembly (660), and an actuator handle assembly (670). Shaft assembly (660) extends distally from actuator handle assembly (670) and stapling head assembly (620) is coupled to a distal end of shaft assembly (660). In brief, actuator handle assembly (670) is operable to actuate a staple driver (not shown) of stapling head assembly (620) to drive a plurality of staples (not shown) out of stapling head assembly (620). The staples are bent to form completed staples by an anvil (640) that is attached at the distal end of instrument (600). Accordingly, tissue may be stapled utilizing instrument (600). Instrument (600) thus operates substantially similar to instrument (10) described above, except for the differences described below.

It should be understood that anvil (640) may be configured an operable in accordance with the teachings above regarding anvil (40). Similarly, stapling head assembly (620) may be configured and operable in accordance with the teachings above regarding stapling head assembly (20). It should also be understood that a knob (698) may be used to adjust the gap distance between a staple forming proximal surface of anvil (640) and a staple ejecting distal surface of stapling head assembly (620), much like knob (98) and knob (398) described above. Unlike instrument (10), instrument (600) of this example includes a pistol grip (674) defined by the housing (672) of handle assembly (670). Pistol grip (674) houses a motor (680), which is operable to actuate stapling head assembly (620) similar to motor (310) described above. As will be described in greater detail below, instrument (600) of the present example also includes a safety trigger assembly (700) and a firing trigger assembly (800) that operate differently from the assemblies described above. As will also be described in greater detail below, instrument (600) of the present example also includes a stop switch (960), which operates substantially similar to stop switch (510) described above. While not shown, motor (680) of the present example is configured to receive power from one or more batteries that are coupled with handle assembly (620), though motor (680) may alternatively receive power in some other fashion (e.g., from an external source via wire, etc.).

B. Exemplary Alternative Firing and Safety Trigger Assemblies

Figure 18:
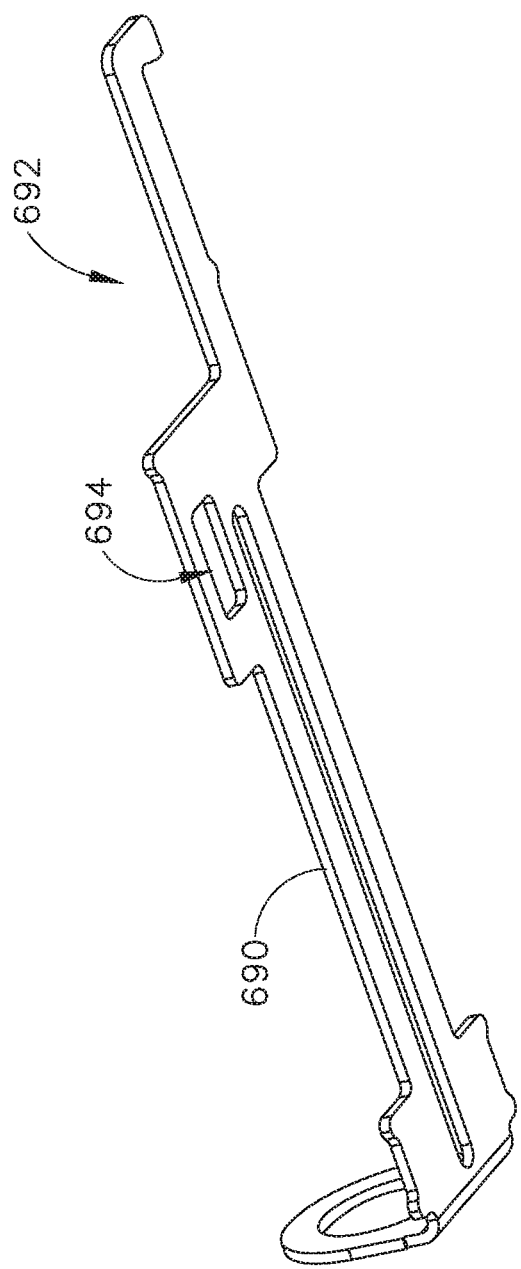
FIG. 18 depicts a perspective view of an indicator bracket of the instrument of FIG. 17.

FIGS. 18-24C show safety trigger assembly (700) and firing trigger assembly (800) in greater detail. FIG. 18 shows an indicator bracket (690) that is configured to selectively enable movement of safety trigger assembly (700) and firing trigger assembly (800). Bracket (690) is configured to translate within handle assembly (670) based on the longitudinal position of anvil (640) in relation to stapling head assembly (620), which is varied by rotation of knob (698) as described above. Like indicator bracket (140) described above, indicator bracket (690) of this example may also be operable to drive an indicator feature that is viewable through a window (602) of handle assembly (670), to thereby provide visual feedback to the operator of instrument (600) to indicate whether and where anvil (640) is within a certain range of distance from stapling head assembly (620). Bracket (690) defines a lateral recess (692) and a slot (694), both of which will be described in greater detail below.

Figure 19:
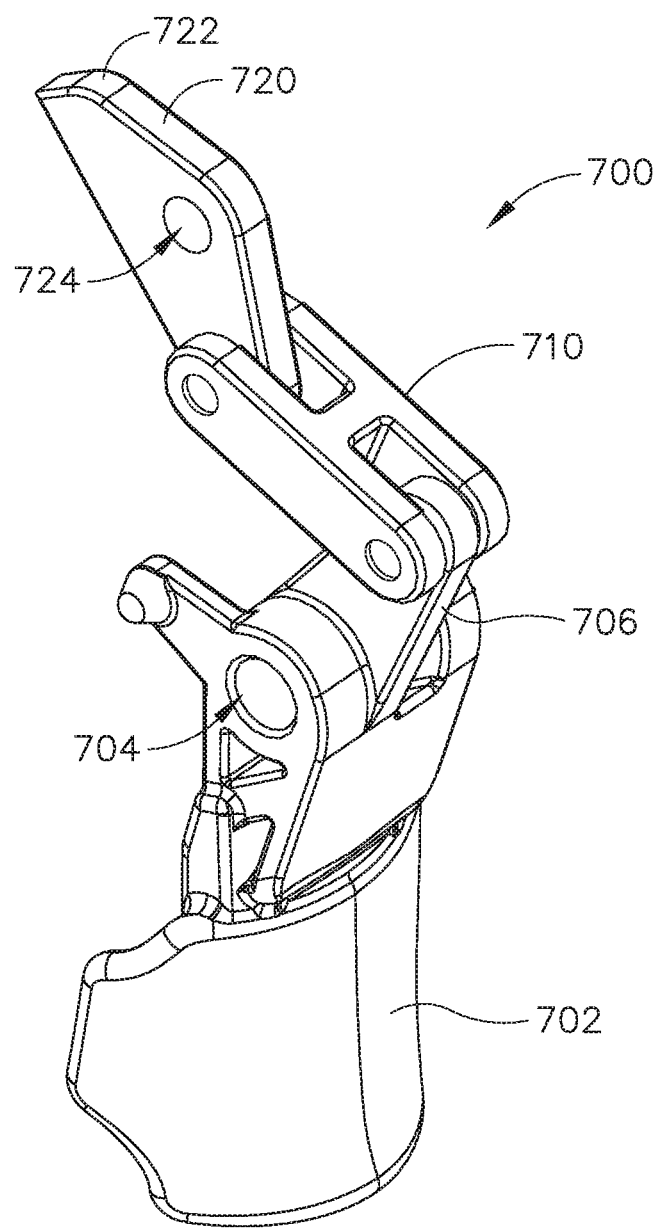
FIG. 19 depicts a perspective view of a safety trigger assembly of the instrument of FIG. 17.
Figure 23A:
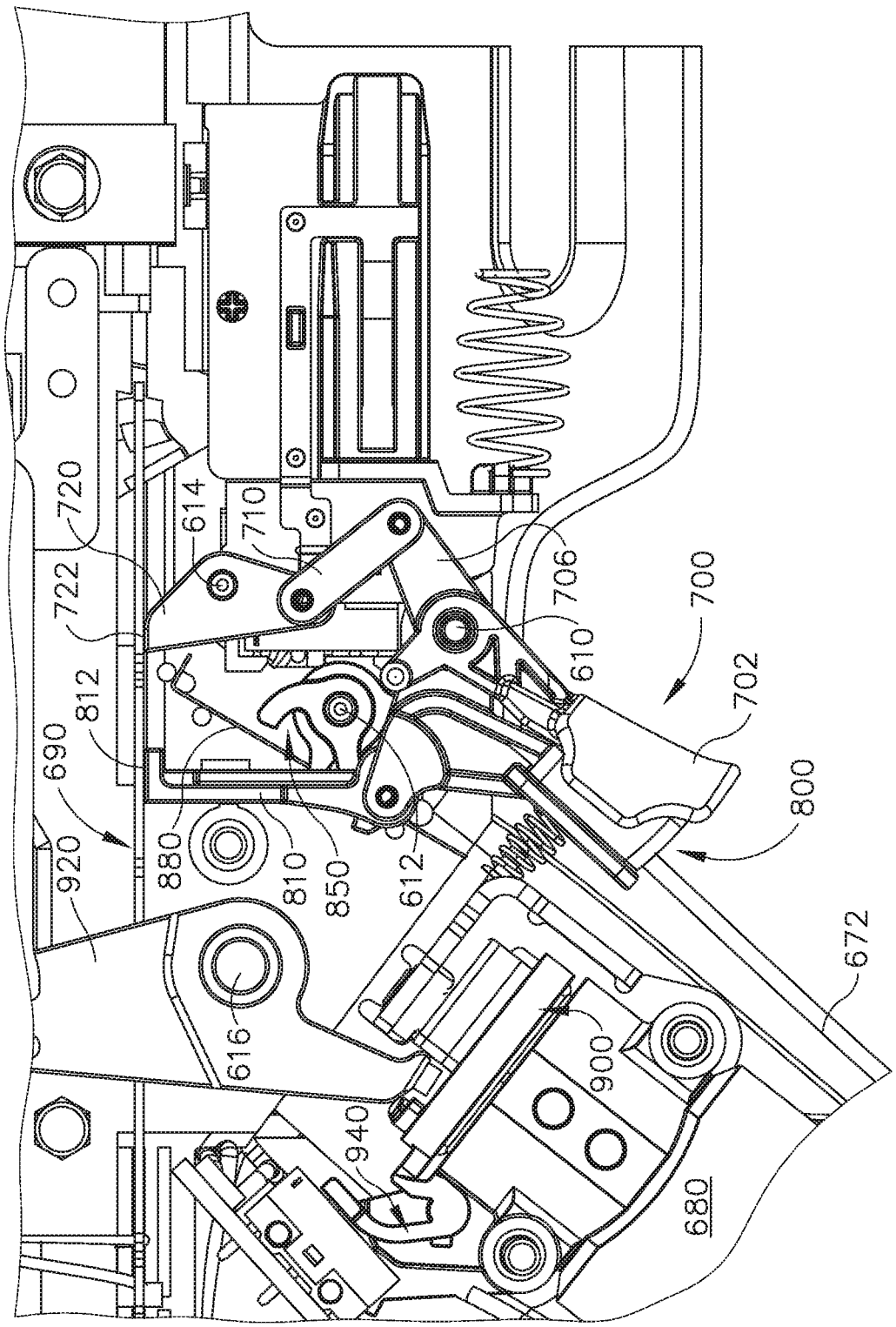
FIG. 23A depicts a perspective view of the safety trigger assembly of FIG. 19 and the firing trigger assembly of FIG. 20, with the safety trigger in a blocking position.
Figure 23C:
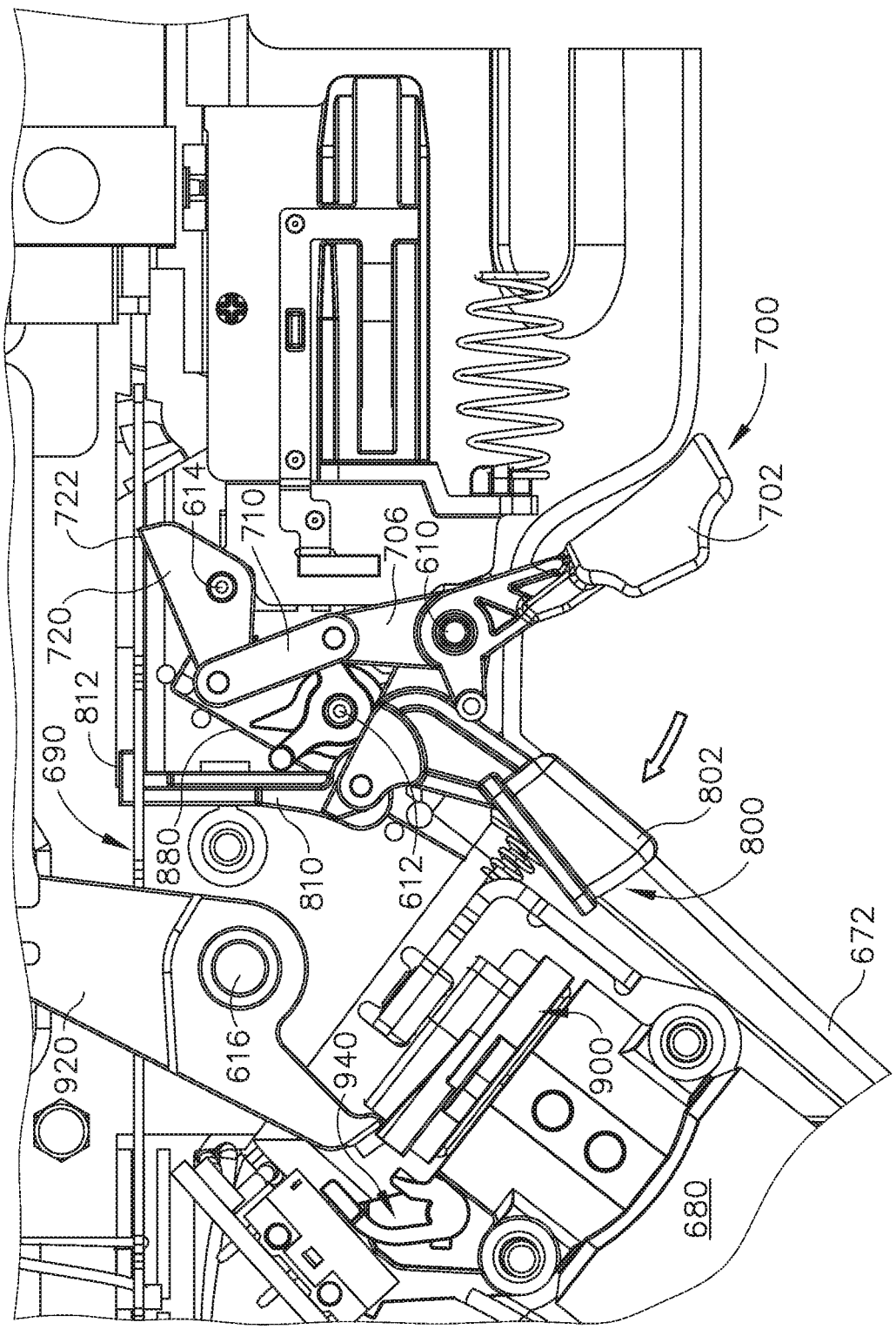
FIG. 23C depicts a perspective view of the safety trigger assembly of FIG. 19 and the firing trigger assembly of FIG. 20, with the safety trigger in the unblocking position and the firing trigger assembly in a fired state.

As best seen in FIG. 19, safety trigger assembly (700) of the present example comprises a button shroud (702), a pivot opening (704) formed in an arm (706), a link (710), and a pivoting boss (720). An integral post (610) of housing (672) of handle assembly (670) is disposed in pivot opening (704), as best seen in FIGS. 23A-23C. Arm (706) is thus operable to pivot about the axis defined by post (610), as will be described in greater detail below. One end of link (710) is pivotally coupled with arm (706) while the other end of link (710) is pivotally coupled with pivoting boss (720). Pivoting boss (720) defines a pivot opening (724) and a free end (722). An integral post (614) of housing (672) of handle assembly (670) is disposed in pivot opening (724), as best seen in FIGS. 23A-23C. Pivoting boss (720) is thus operable to pivot about the axis defined by post (614), as will be described in greater detail below.

Safety trigger assembly (700) is configured such that button shroud (702) selectively covers or blocks a trigger button (802) of firing trigger assembly (800), as shown in FIG. 23A. When button shroud (702) blocks trigger button (802), the operator is unable to depress trigger button (802), such that the operator is unable to actuate stapling head assembly (620). The operator must therefore move button shroud (702) distally as shown in FIG. 23B in order to access trigger button (802) for firing stapling head assembly (620). However, indicator bracket (690) is configured to prevent such distal movement of button shroud (702) unless anvil (640) is within a suitable longitudinal range of stapling head assembly (620). In particular, the body of indicator bracket (690) is configured to engage free end (722) of pivoting boss (720), thereby preventing rotation of pivoting boss (720) about post (614), when anvil (640) is outside of the suitable longitudinal range of stapling head assembly (620). Button shroud (702) and arm (706) are unable to rotate about post (610) when the body of indicator bracket (690) blocks pivoting boss (720) in this way. Once anvil (640) reaches a suitable longitudinal range of stapling head assembly (620), lateral recess (692) provides sufficient clearance for free end (722), thereby enabling rotation of pivoting boss (720) about post (614). Indicator bracket (690) thus allows button shroud (702) and arm (706) to rotate about post (610) when anvil (640) reaches a suitable longitudinal range of stapling head assembly (620).

Figure 20:
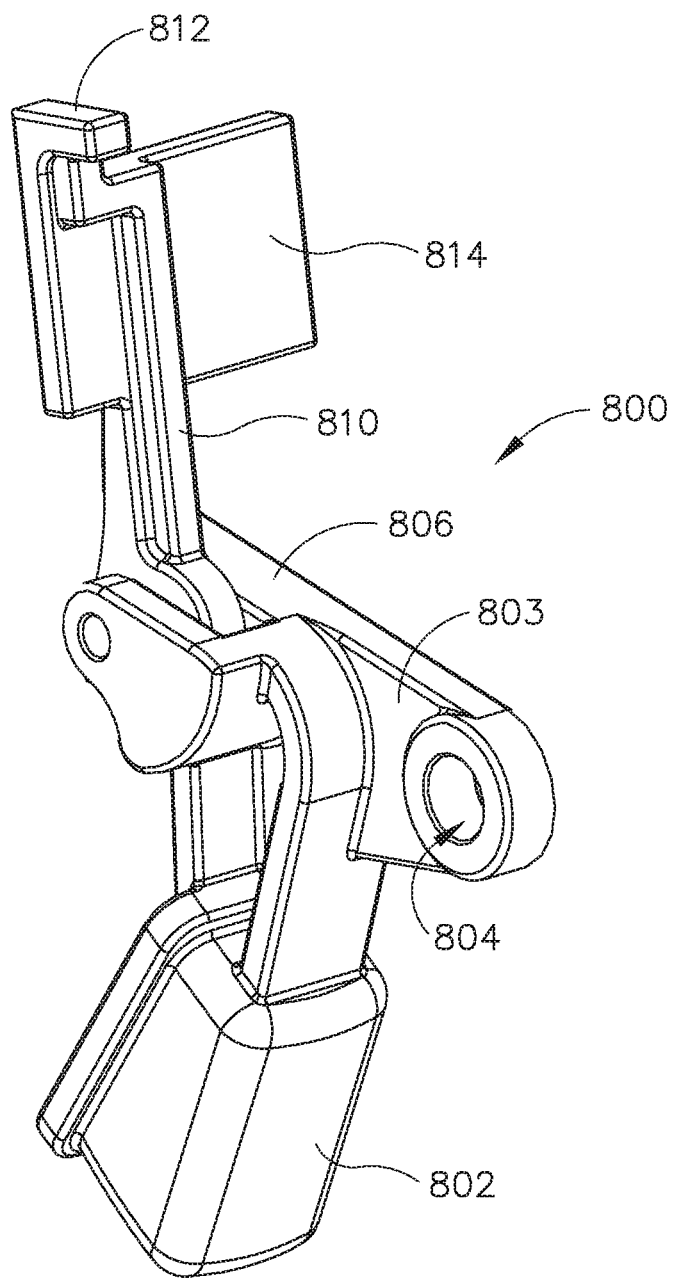
FIG. 20 depicts a perspective view of a firing trigger assembly of the instrument of FIG. 17.
Figure 24A:
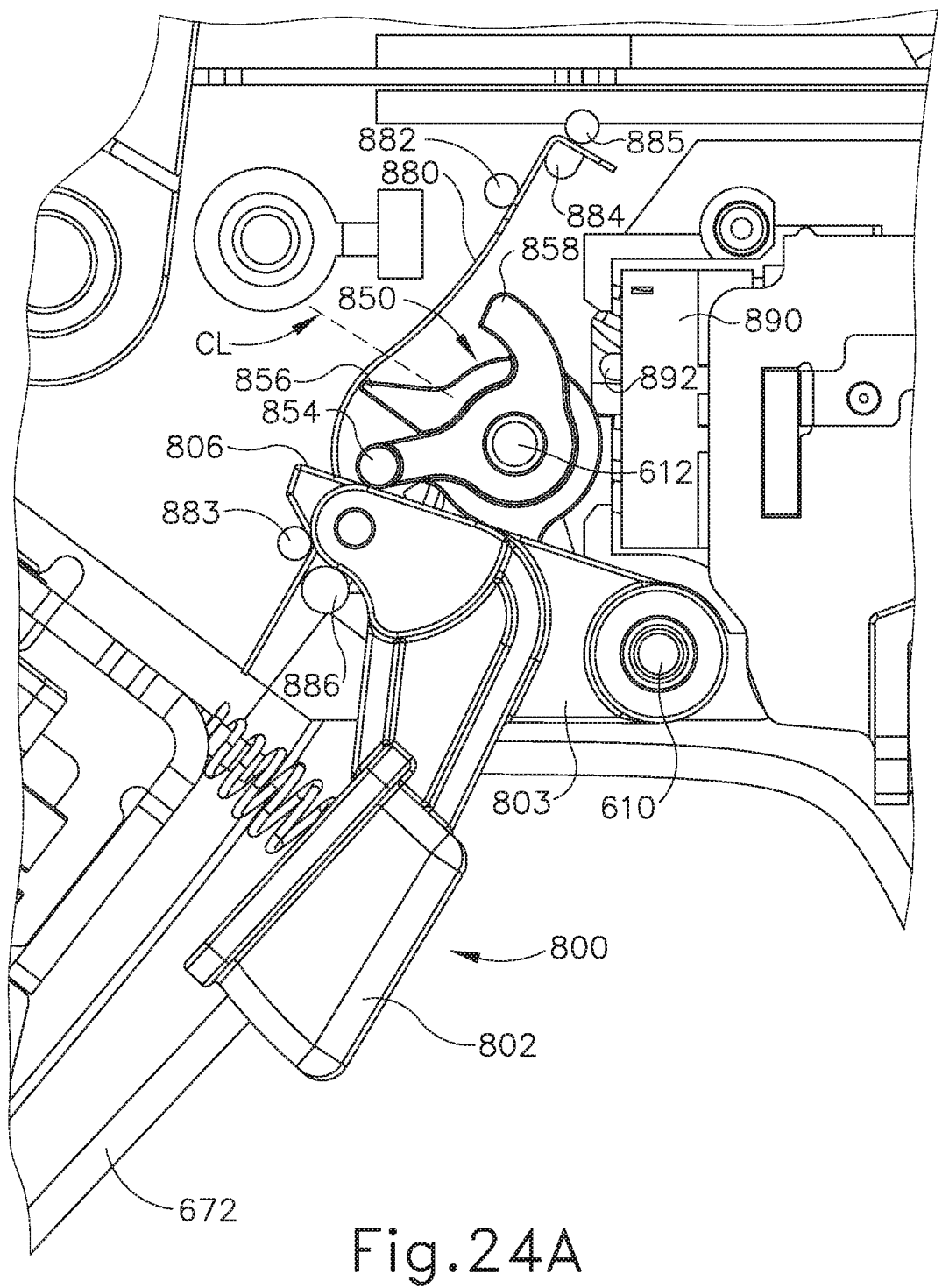
FIG. 24A depicts a side elevational view of the assembly of FIG. 21, with the firing trigger in an unfired state.
Figure 24B:
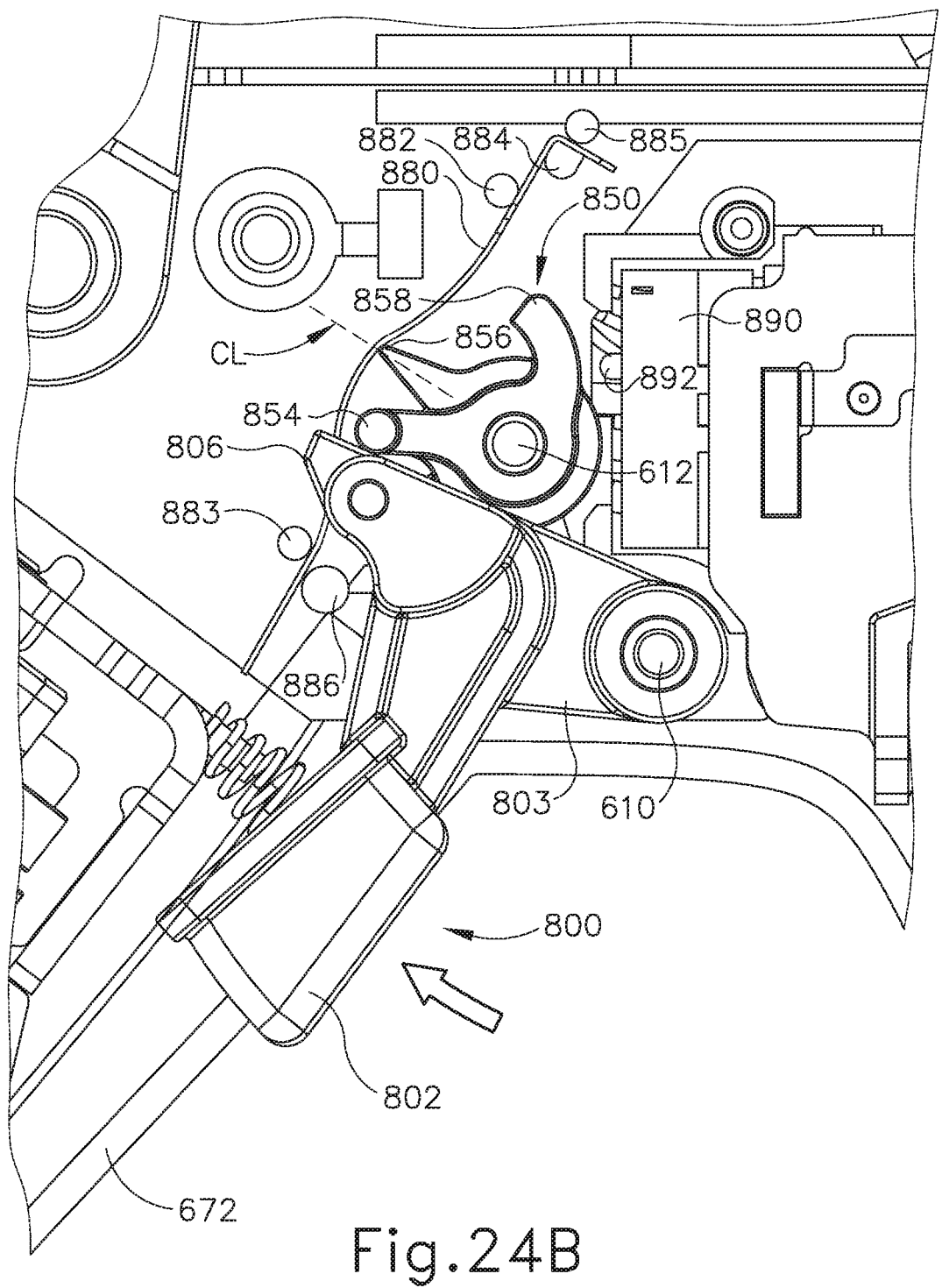
FIG. 24B depicts a side elevational view of the assembly of FIG. 21, with the firing trigger in a fired state and the rotary actuator in a partially actuated state.
Figure 24C:
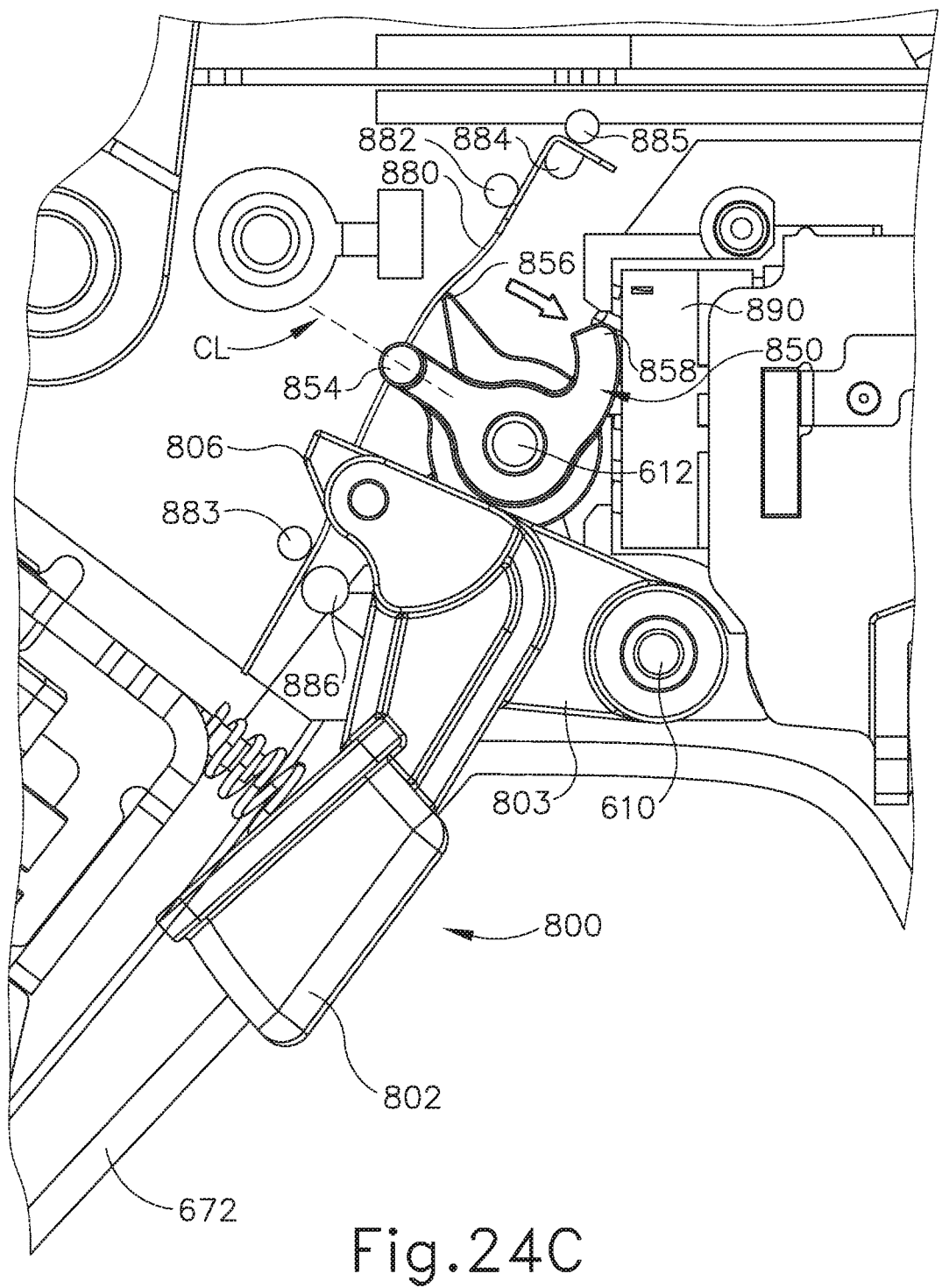
FIG. 24C depicts a side elevational view of the assembly of FIG. 21, with the firing trigger in a fired state and the rotary actuator in a fully actuated state.

As best seen in FIG. 20, firing trigger assembly (800) of the present example comprises a trigger button (802), a pivot opening (804) formed in an arm (803), and a translating boss (810). Post (610) of housing (672) of handle assembly (670) is disposed in pivot opening (804), as best seen in FIGS. 24A-24C. Arm (803) is thus operable to pivot about the axis defined by post (610), as will be described in greater detail below. Arm (803) includes a cam surface (806), which will also be described in greater detail below. Translating boss (810) is pivotally coupled with arm (803) and includes a free end (812) and a guide feature (814). Guide feature (814) is engaged with housing (672) of handle assembly (670) such that translating boss (810) translates vertically along a liner path in response to pivoting of arm (803) about post (610). This pivoting of arm (803) also actuates stapling head assembly (620) as will be described in greater detail below.

In addition to selectively blocking actuation of safety trigger assembly (700), indicator bracket (690) is also operable to selectively block actuation of firing trigger assembly (800). In particular, the body of indicator bracket (690) is configured to engage free end (812) of translating boss (810), thereby preventing upward translation of translating boss (810), when anvil (640) is outside of the suitable longitudinal range of stapling head assembly (620). Trigger button (802) and arm (803) are unable to rotate about post (610) when the body of indicator bracket (690) blocks translating boss (810) in this way. Once anvil (640) reaches a suitable longitudinal range of stapling head assembly (620), slot (694) provides sufficient clearance for free end (812), thereby enabling upward translation of translating boss (810). Indicator bracket (690) thus allows trigger button (802) and arm (803) to rotate about post (610) when anvil (640) reaches a suitable longitudinal range of stapling head assembly (620).

FIGS. 23A-23C show an exemplary sequence of operation of safety trigger assembly (700) and firing trigger assembly (800). In FIG. 23A, safety trigger assembly (700) is configured to cover or block trigger button (802), thereby preventing actuation of firing trigger assembly (800). This further prevents actuation of stapling head assembly (620). In FIG. 23B, safety trigger assembly (700) has been actuated to uncover or unblock trigger button (802), thereby enabling actuation of firing trigger assembly (800). In FIG. 23C, firing trigger assembly (800) has been actuated, thereby actuating stapling head assembly (620). Further details regarding the component interactions that take place during the transition from the state shown in FIG. 23B to the state shown in FIG. 23C will be described below with reference to FIGS. 24A-24C.

Figure 21:
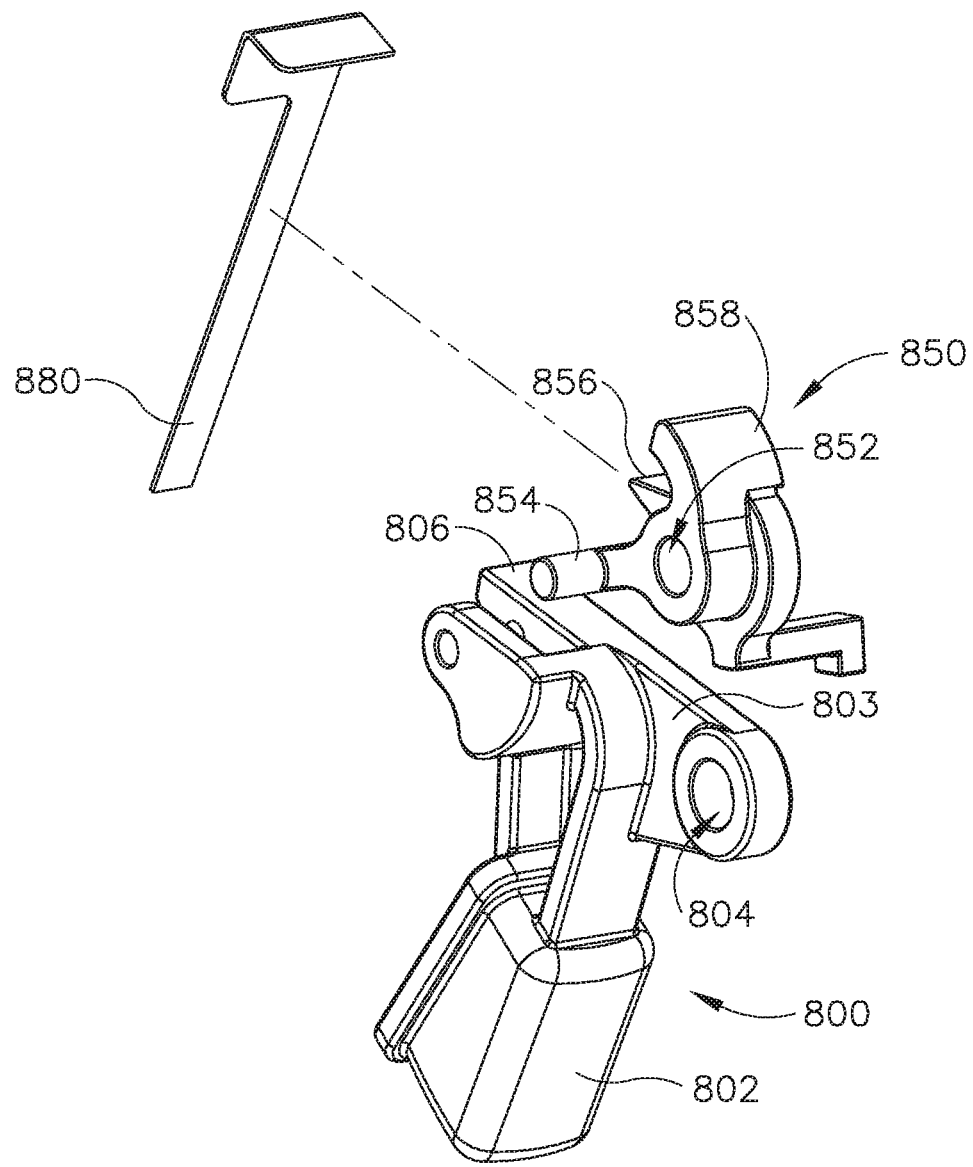
FIG. 21 depicts a perspective view of a portion of the firing trigger assembly of FIG. 20 with a rotary actuator and a leaf spring.
Figure 22:
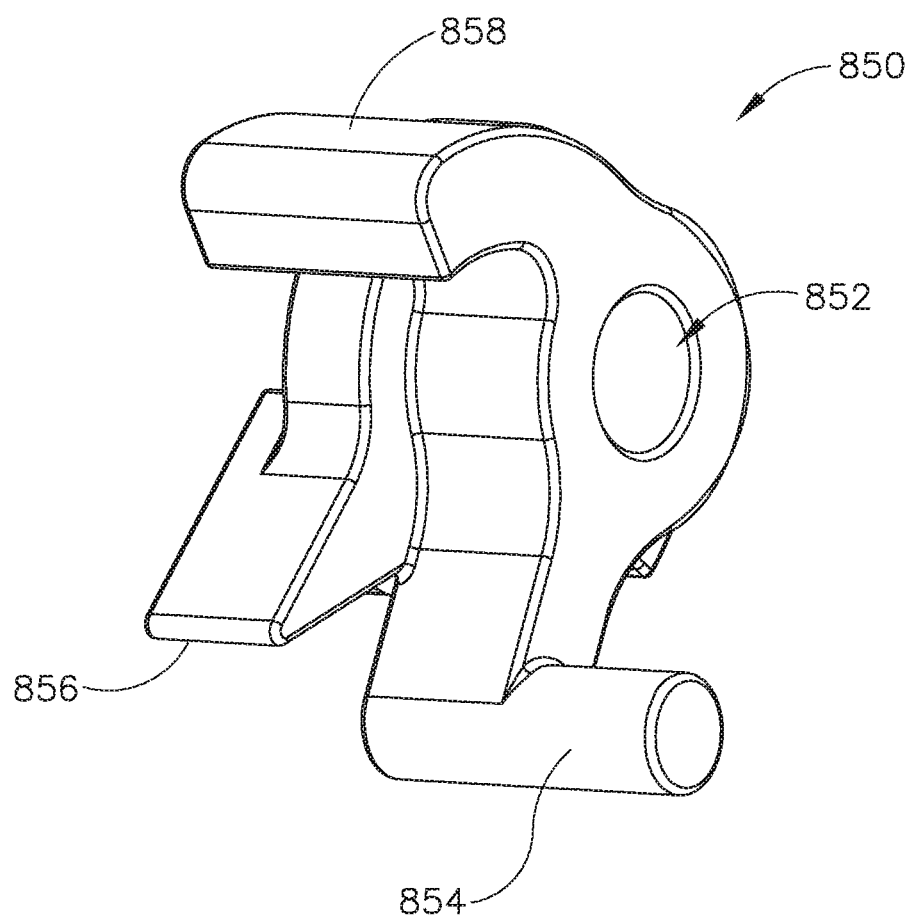
FIG. 22 depicts a perspective view of the rotary actuator of FIG. 21.

FIGS. 21-22 show a rotary actuator (850) that firing trigger assembly (800) is operable to set in motion to fire stapling head assembly (620). It should be noted that translating boss (810) is omitted from FIG. 21 for clarity. Rotary actuator (850) defines an opening (852). Post (612) of housing (672) of handle assembly (670) is disposed in pivot opening (852), as best seen in FIGS. 24A-24C. Rotary actuator (850) is thus operable to rotate about an axis defined by post (612), as will be described in greater detail below. As best seen in FIGS. 21-22, rotary actuator (850) includes a laterally projecting cam pin (854), an engagement fin (856), and an actuating arm (858). Cam pin (854) is configured to engage cam surface (806) of arm (803) of firing trigger assembly (800). Engagement fin (856) is configured to engage a leaf spring (880). Actuating arm (858) is configured to engage a firing switch actuator (892).

Leaf spring (880) of the present example is formed by a resilient strip of metal, though it should be understood that various kinds of resilient members may be used. As best seen in FIGS. 24A-24C, leaf spring (880) is retained in housing (672) of handle assembly (670) by a set of bosses (882, 883, 884, 885, 886). Bosses (882, 883, 884, 885, 886) are configured to maintain the position of leaf spring (880) in housing (672); while allowing leaf spring (880) to deform during a firing sequence as shown in FIGS. 24A-24C. In the present example, engagement fin (856) remains engaged with leaf spring (880) throughout this entire firing sequence. In some other variations, engagement fin (856) is disengaged from leaf spring (880) during at least one stage of operation (e.g., before firing, after firing, etc.). It should be understood that leaf spring (880) is laterally spaced from cam pin (854), such that cam pin (854) rotates past leaf spring (880) during the firing sequence without engaging leaf spring (880).

Firing switch actuator (892) is coupled with a firing switch enclosure (890), which is fixedly mounted in housing (672) of handle assembly (670). Firing switch actuator (892) is operable to selectively activate motor (680), to thereby actuate stapling head assembly (620). Firing switch (356), as described above with respect to control system (300), is incorporated into firing trigger assembly (800). It should also be understood that firing switch actuator (892) may be configured an operable in accordance with the above teachings of firing switch (500).

FIGS. 24A-24C show an exemplary firing sequence carried out by firing trigger assembly (800) and rotary actuator (850). It should be noted that translating boss (810) is omitted from FIGS. 24A-24C for clarity. FIG. 24A shows firing trigger assembly (800) in a pre-fired position. In this state, cam pin (854) of rotary actuator (850) rests against cam surface (806) of firing trigger assembly (800). Engagement fin (856) is engaged with leaf spring (880), such that leaf spring (880) is slightly deformed by engagement fin (856). Engagement fin (856) engages leaf spring (880) at a location below a center line (CL), which is defined as a line extending transversely through leaf spring (880) at a point that is mid-way between bosses (882, 883). Engagement fin (856) is thus "under center" in this state. Actuating arm (858) is substantially spaced from firing switch actuator (892), such that firing switch actuator (892) is in a non-actuated state.

FIG. 24B shows firing trigger assembly (800) in a partially fired position. In this state, firing button (802) has been fully depressed, such that rotary actuator (850) has been rotated about post (612) due to a camming interaction between cam surface (806) and cam pin (854). Engagement fin (856) is still engaged with leaf spring (880), such that leaf spring (880) is still being deformed by engagement fin (856). At this stage, engagement fin (856) has just passed the center line (CL), such that engagement fin (856) has just reached an "over center" state. At this stage, the resilience of leaf spring (880) continues to drive rotary actuator (850) to rotate about post (612), with cam pin (854) disengaging cam surface (806). Actuating arm (858) is still spaced from firing switch actuator (892), such that firing switch actuator (892) is still in a non-actuated state at the stage shown in FIG. 24B.

FIG. 24C shows firing trigger assembly (800) in a fully fired position. In this state, firing button (802) has not moved further past the position shown in FIG. 24B. However, the resilience of leaf spring (880) has driven rotary actuator (850) to rotate about post (612) to a point where actuating arm (858) has actuated firing switch actuator (892), thereby activating motor (680) to drive stapling head assembly (620). Leaf spring (880) remains engaged with engagement fin (856) at this stage, such that engagement fin (856) continues to deform leaf spring (880) and leaf spring (880) biases actuating arm (858) into continued engagement with firing switch actuator (892).

It should be understood from the foregoing that firing button (802) is operable to drive rotary actuator (850) through a first range of motion, while engagement fin (856) is in an "under center" relationship with leaf spring (880). Once engagement fin (856) reaches an "over center" relationship with leaf spring (880), leaf spring (880) drives rotary actuator (850) through a second range of motion. In this second range of motion, rotary actuator (850) is operationally decoupled from firing button (802), and firing switch actuator (892) is actuated. It should therefore be understood that the operator will not be able to prevent actuation of firing switch actuator (892) once rotary actuator (850) reaches the second range of motion. In other words, releasing a grip on firing button (802) will not stop further rotation of rotary actuator (850) once rotary actuator reaches an "over center" state with respect to leaf spring (880).

C. Exemplary Stop Switch Assembly

Figure 25:
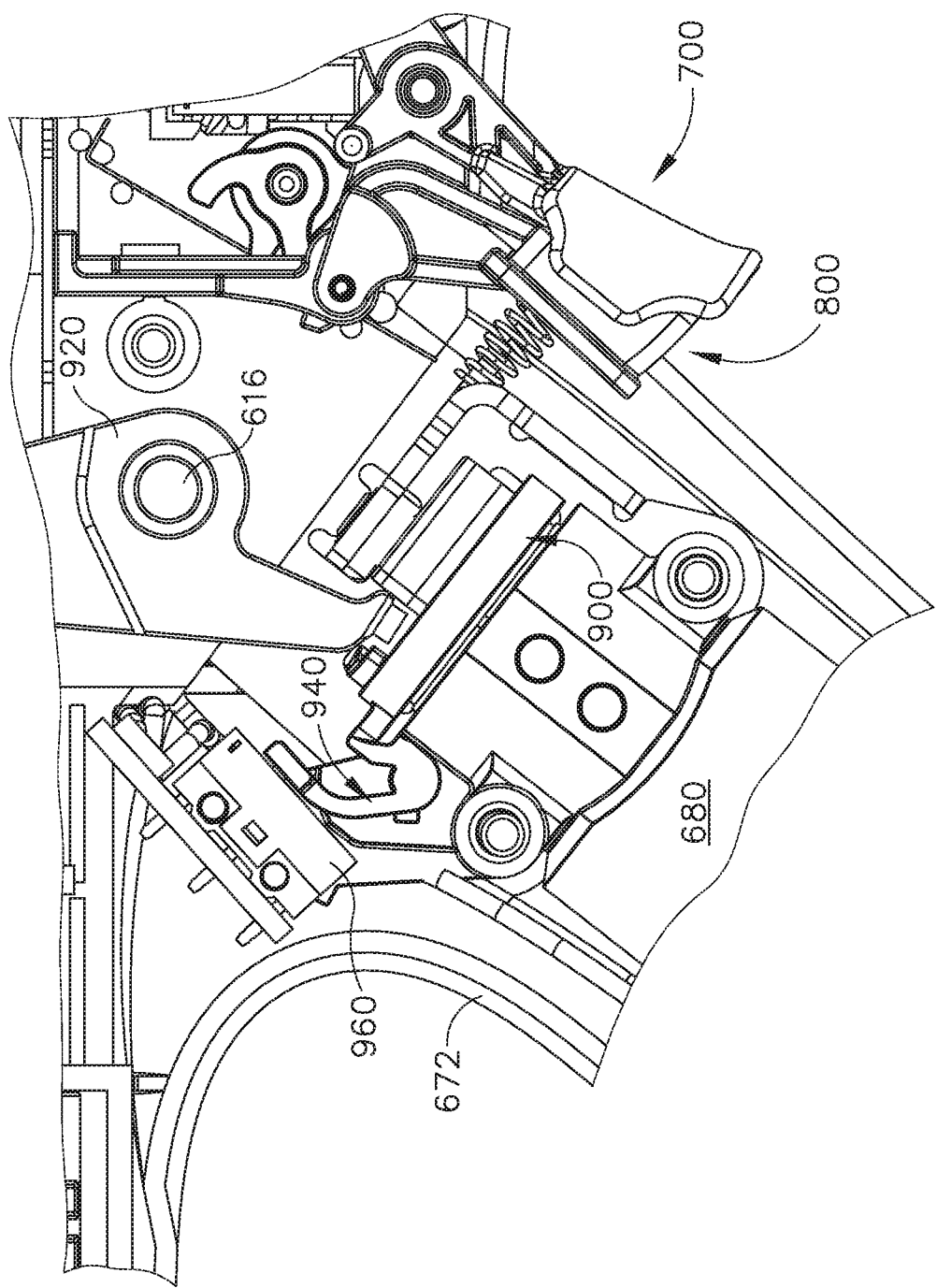
FIG. 25 depicts a side elevational view of a stop switch assembly of the instrument of FIG. 17.

The examples described above with respect to FIGS. 14-16 include a stop switch (510) that is operable to short circuit motor (210) to thereby prevent motor (210) from further activation. FIGS. 25-28B show various features that may be used to trigger such a stop switch (510) at the completion of a firing stroke of stapling head assembly (620). In particular. FIG. 25 shows a stop switch enclosure (960), a cam member (900), and a rocker member (940). Stop switch enclosure (960) is fixedly mounted in housing (672) of handle assembly (670); and includes a stop switch actuator (962) as best seen in FIG. 28A. While stop switch actuator (962) is analogous to stop switch (510) in the present example, it should be understood that stop switch actuator (962) may provide any other suitable operability. As will be described in greater detail below, cam member (900) is operable to selectively drive rocker member (940) into engagement with stop switch actuator (962) upon completion of a drive stroke by motor (680) and stapling head assembly (620).

Figure 26:
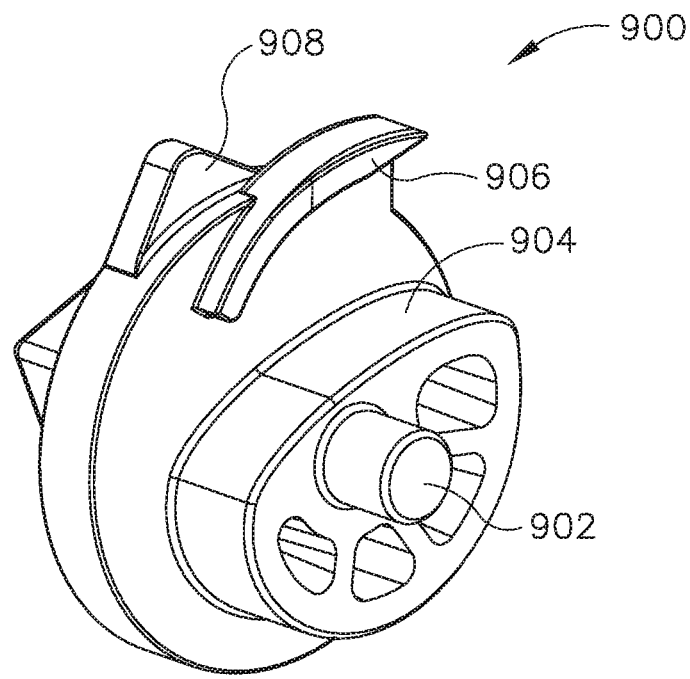
FIG. 26 depicts a perspective view of a cam member of the stop switch assembly of FIG. 25.

As best seen in FIG. 26, cam member (900) of the present example comprises an integral shaft (902), a first cam feature (904), a second cam feature (906), and a third cam feature (908). Shaft (902) is coupled with motor (680) such that motor (680) drives cam member (900) to rotate about the axis defined by shaft (902). First cam feature (904) is coupled with a pivoting actuator (920) such that first cam feature (904) drives pivoting actuator (920) to rotate in a first direction during a first 270° of travel by cam member (900). Pivoting actuator (920) drives a staple driver and knife of stapling head assembly (620) distally during this rotation of pivoting actuator (920) in the first direction. Second cam feature (906) is coupled with pivoting actuator (920) such that second cam feature (906) drives pivoting actuator (920) to rotate in a second direction during a subsequent 90° of travel by cam member (900). Pivoting actuator (920) drives a staple driver and knife of stapling head assembly (620) proximally during this rotation of pivoting actuator (920) in the second direction. It should be understood that pivoting actuator (920) of this example may operate similar to pivoting actuator (312) as described above. It should also be understood that pivoting actuator (920) and cam member (900) may be operable in accordance with at least some of the teachings of U.S. patent application Ser. No. 14/033,688, entitled SURGICAL STAPLER WITH ROTARY CAM DRIVE AND RETURN, filed Sep. 23, 2013, published as U.S. Pub. No. 2015/0083772 on Mar. 26, 2015, now abandoned, the disclosure of which is incorporated by reference herein. While the full 360° revolution of cam member (900) is allocated as 270° for distal motion of the staple driver and knife; and the remaining 90° for proximal motion of the staple driver and knife, it should be understood that the allocation may be made in any other suitable fashion (e.g., 180° for distal motion and 180° for proximal motion, etc.). It should also be understood that a full range of distal and proximal travel may be provided by less than 360° of rotation of cam member (900).

Figure 27:
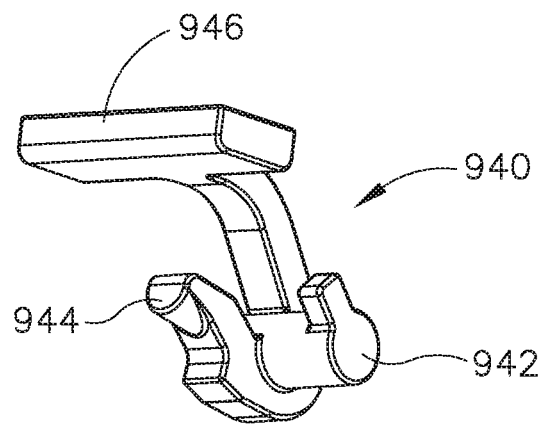
FIG. 27 depicts a perspective view of a rocker member of the stop switch assembly of FIG. 25.
Figure 28A:
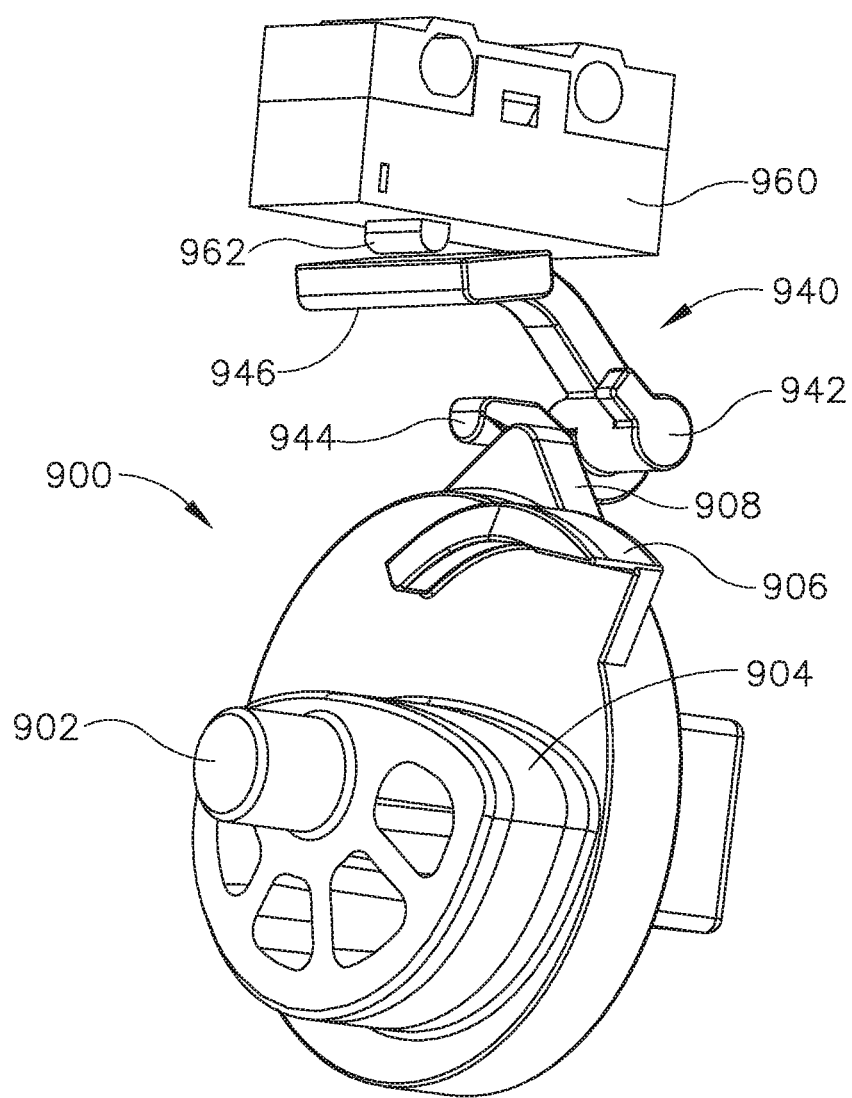
FIG. 28A depicts a perspective view of the stop switch assembly of FIG. 25 in a pre-fired state.
Figure 28B:
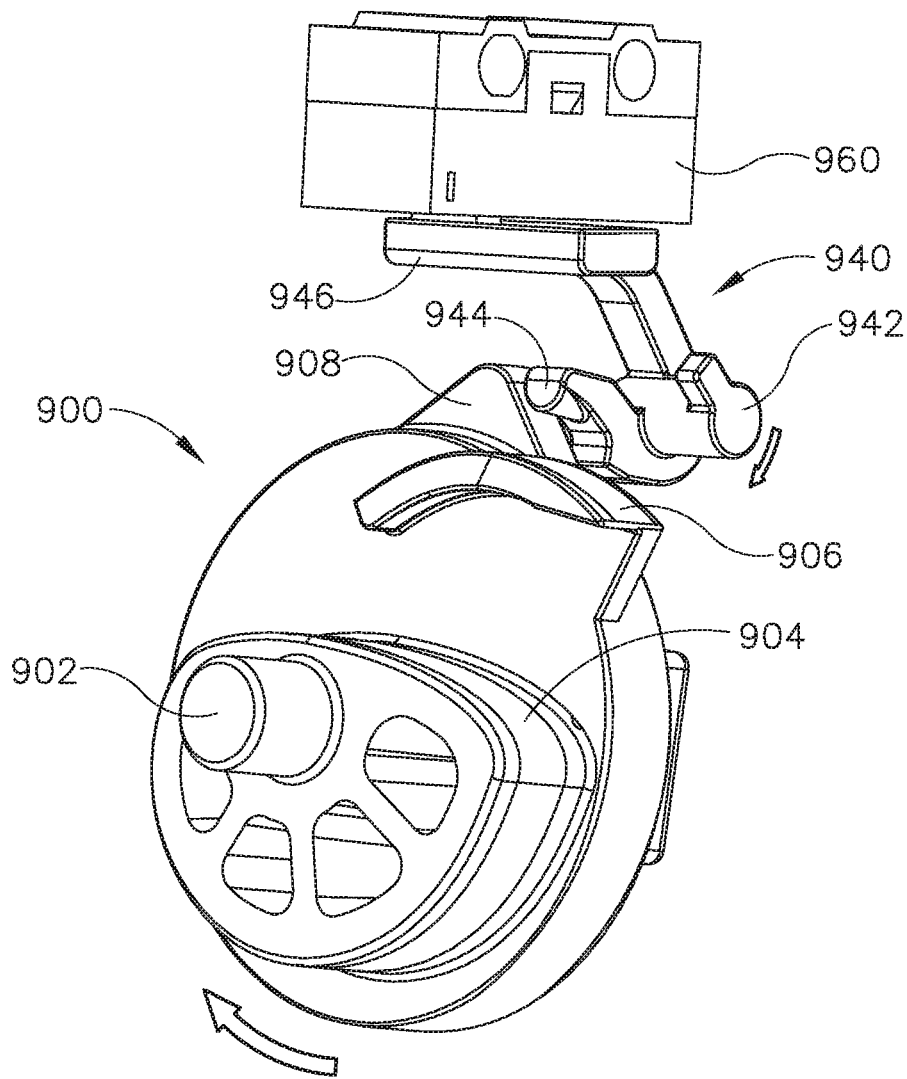
FIG. 28B depicts a perspective view of the stop switch assembly of FIG. 25 in a fired state.

As best seen in FIG. 27, rocker member (940) of the present example comprises an integral pin (942), a cam arm (944), and an actuator arm (946). Pin (942) is pivotally engaged with housing (672) of handle assembly, such that rocker member (940) is rotatable relative to housing (972) about an axis defined by pin (942). Cam arm (944) is configured to engage third cam feature (908) of cam member (900). Actuator arm (946) is configured to engage stop switch actuator (962). FIGS. 28A-28B show rocker member (940) interacting with cam member (900) and stop switch actuator (962) in an exemplary drive sequence. In particular, FIG. 28A depicts cam member (900) at a rotational position before stapling head assembly (620) is actuated. In this state, rocker member (940) is in a first rotational position about the axis defined by pin (942), such that actuator arm (946) is not depressing stop switch actuator (962). When motor (680) is activated by firing switch actuator (892), motor (680) rotates cam member (900) to the position shown in FIG. 28B. Cam member (900) actuates stapling head assembly (620) while traveling from the position shown in FIG. 28A to the position shown in FIG. 28B. In addition, third cam feature (908) engages cam arm (944) as cam member (900) rotates to the position shown in FIG. 28A. In particular, third cam feature (908) bears against cam arm (944), causing rocker member (940) to rotate about the axis defined by pin (942), such that actuator arm (946) depresses stop switch actuator (962). In some versions, depression of stop switch actuator (962) results in the circuit shown in FIG. 16, where motor (210, 680) is short circuited and battery (230) is coupled with power sink (240). Cam member (900), rocker member (940), and stop switch actuator (962) thus cooperate to effectively cut off power to motor (680) at the end of a firing stroke and battery (230) continues to be discharged. Other suitable ways in which a stop switch actuator (962) may be triggered will be apparent to those of ordinary skill in the art in view of the teachings herein.

It should also be understood that power sink (240) may be coupled with battery (230) before stop switch actuator (962) is depressed. For instance, power sink (240) may be coupled with battery (230) as soon as a battery pack containing battery (230) is coupled with actuator handle assembly (670). Other suitable conditions that may result in coupling of power sink (240) with battery (230) will be apparent to those of ordinary skill in the art in view of the teachings herein. Of course, power sink (240) may simply be omitted.

V. Miscellaneous

In the examples shown in FIGS. 8-9 and 13A-13C, motors (210, 310) are oriented coaxially with drive shafts (240, 340, 440) and parallel to shaft assembly (60). However, motors (210, 310) may instead positioned in other suitable orientations. For instance, in some versions, motors (210, 310) may be positioned perpendicularly or at any oblique angle in relation to a longitudinal axis of shaft assembly (60). In some such versions, motors (210, 310) may be positioned within a pistol grip provided by an alternative version of handle assembly (70). Motors (210, 310) may be configured to convey rotational movement along non-parallel axes by coupling motors (210, 310) to shafts drive assemblies (211, 311) through bevel gears, etc.; and/or using any other suitable structure(s). By way of example only, motors (210, 310) may transfer motion to drive assemblies (211, 311) in accordance with the teachings of U.S. patent application Ser. No. 14/033,688, entitled SURGICAL STAPLER WITH ROTARY CAM DRIVE AND RETURN, filed Sep. 23, 2013, published as U.S. Pub. No. 2015/0083772 on Mar. 26, 2015, now abandoned, the disclosure of which is incorporated by reference herein. Similarly, handle assembly (70) may provide a perpendicularly oriented or obliquely oriented pistol grip in accordance with the teachings of U.S. patent application Ser. No. 14/033,688, entitled SURGICAL STAPLER WITH ROTARY CAM DRIVE AND RETURN, filed Sep. 23, 2013, now abanoned, published as U.S. Pub. No. 2015/0083772 on Mar. 26, 2015, the disclosure of which is incorporated by reference herein. Other suitable ways in which obliquely oriented motors (210, 310) may be incorporated into the instruments described herein will be apparent to those of ordinary skill in the art in view of the teachings herein.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, now U.S. Pat. No. 8,408,439, issued Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body;
   (b) an end effector extending distally from the body, wherein the end effector comprises a stapling assembly operable to drive staples into tissue; and
   (c) a control system in communication with the end effector, wherein the control system comprises:
      (i) a motor,
      (ii) a rotary drive member coupled with the motor and having a cam feature, wherein the rotary drive member is rotatable by the motor through a range of motion to actuate the stapling assembly to perform a firing stroke,
      (iii) a movable member, and
      (iv) a stop switch in communication with the motor, wherein the stop switch is configured to transition between:
         (A) a first state in which the stop switch permits activation of the motor and initiation of the firing stroke in response to a user input, and
         (B) a second state in which the stop switch deactivates the motor to cease actuation of the stapling assembly,
      wherein the cam feature is configured to drive the movable member into engagement with the stop switch and thereby transition the stop switch from the first state to the second state when the rotary drive member completes the range of motion,
      wherein the movable member is configured to remain stationary while the rotary drive member rotates through a portion of the range of motion.

2. The apparatus of claim 1, wherein the moveable member is configured to remain stationary as the rotary drive member rotates through a first portion of the range of motion, wherein the moveable member is configured to move into engagement with the stop switch as the rotary drive member rotates through a second portion of the range of motion.

3. The apparatus of claim 1, wherein the moveable member comprises a rocker member, wherein the rocker member is rotatable about an axis.

4. The apparatus of claim 1, wherein the moveable member includes a first arm configured to engage the cam feature of the rotary drive member, and a second arm configured to engage the stop switch.

5. The apparatus of claim 1, further comprising a pivoting member operatively coupled with the stapling assembly, wherein the rotary drive member is configured to pivot the pivoting member in a first direction to actuate the stapling assembly through a first portion of the firing stroke, wherein the rotary drive member is further configured to pivot the pivoting member in a second direction to actuate the stapling assembly through a second portion of the firing stroke.

6. The apparatus of claim 1, wherein the cam feature comprises a first cam feature, wherein the rotary drive member further comprises a second cam feature configured to actuate the stapling assembly through at least a first portion of the firing stroke.

7. The apparatus of claim 6, wherein the rotary drive member further comprises a third cam feature configured to actuate the stapling assembly through a second portion of the firing stroke.

8. The apparatus of claim 7, wherein at least a portion of the third cam feature is circumferentially offset from the second cam feature about a rotational axis of the rotary drive member.

9. The apparatus of claim 8, further comprising a pivoting member operatively coupled with the stapling assembly, wherein the second cam feature is configured to pivot the pivoting member in a first direction to actuate the stapling assembly through the first portion of the firing stroke, wherein the third cam feature is configured to pivot the pivoting member in a second direction to actuate the stapling assembly through the second portion of the firing stroke.

10. The apparatus of claim 1, wherein the motor, the rotary drive member, and the stop switch are housed within the body.

11. The apparatus of claim 1, wherein the control system further comprises a firing trigger, wherein the motor is configured to activate in response to actuation of the firing trigger.

12. The apparatus of claim 1, wherein the control system further comprises:
   (a) a power source operable to activate the motor, and
   (b) a power sink,
   wherein the stop switch is configured to decouple the power source from the motor and couple the power source with the power sink when the stop switch transitions from the first state to the second state.

13. The apparatus of claim 1, wherein the range of motion of the rotary drive member consists of a single revolution about a rotational axis.

14. An apparatus, comprising:
   (a) a body;
   (b) an end effector extending distally from the body, wherein the end effector comprises a stapling assembly operable to drive staples into tissue; and
   (c) a control system in communication with the end effector, wherein the control system comprises:
      (i) a motor,
      (ii) a first moveable member, wherein the first moveable member is rotatable by the motor about a first axis to actuate the stapling assembly to perform a firing stroke,
      (iii) a second moveable member, wherein the second moveable member is rotatable about a second axis offset from the first axis, and
      (iv) a stop switch in communication with the motor, wherein the stop switch is operable to selectively deactivate the motor to cease actuation of the stapling assembly,
   wherein the first moveable member is rotatable by the motor to contact and drive the second moveable member into engagement with the stop switch to thereby deactivate the motor upon completion of the firing stroke.

15. The apparatus of claim 14, wherein the first axis extends in a first direction, wherein the second axis extends in a second direction.

16. The apparatus of claim 14, wherein the first moveable member includes a cam feature operable to engage the second moveable member to thereby drive the second moveable member into engagement with the stop switch.

17. The apparatus of claim 14, wherein the second axis is transverse relative to the first axis.

18. An apparatus, comprising:
(a) a body;
(b) an end effector extending distally from the body, wherein the end effector comprises a stapling assembly operable to drive staples into tissue; and
(c) a control system in communication with the end effector, wherein the control system comprises:
  (i) a motor,
  (ii) a power source operable to activate the motor,
  (iii) a rotary drive member coupled with the motor, wherein the rotary drive member is rotatable by the motor through a single revolution to actuate the stapling assembly to perform a firing stroke,
  (iv) an actuator member, wherein the actuator member is moveable by the rotary drive member from a first position to a second position upon completion of the revolution, and
  (v) a stop switch, wherein the actuator member is configured to engage the stop switch in the second position,
wherein the stop switch is configured to couple the power source with the motor to thereby permit activation of the motor and initiation of the firing stroke when the actuator member is in the first position,
wherein the stop switch is further configured to decouple the power source from the motor and thereby deactivate the motor when the actuator member is in the second position.

19. The apparatus of claim 18, wherein the rotary drive member includes a cam feature operable to engage and drive the actuator member from the first position to the second position.

20. The apparatus of claim 18, wherein the rotary drive member is rotatable about a first axis, wherein the actuator member is rotatable about a second axis offset from the first axis.

* * * * *